US008883716B2

(12) United States Patent
Shafer

(10) Patent No.: US 8,883,716 B2
(45) Date of Patent: *Nov. 11, 2014

(54) METHOD FOR TREATING DAMAGED TISSUE OF THE CNS

(75) Inventor: Lisa L. Shafer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

This patent is subject to a terminal disclaimer.

(21) Appl. No.: 13/313,216

(22) Filed: Dec. 7, 2011

(65) Prior Publication Data

US 2012/0143272 A1    Jun. 7, 2012

Related U.S. Application Data

(62) Division of application No. 11/000,856, filed on Dec. 1, 2004, now Pat. No. 8,093,205.

(60) Provisional application No. 60/526,405, filed on Dec. 1, 2003, provisional application No. 60/526,318, filed on Dec. 1, 2003.

(51) Int. Cl.

| A61K 38/00 | (2006.01) |
| A61K 38/18 | (2006.01) |
| C07K 14/475 | (2006.01) |
| C07K 14/48 | (2006.01) |
| C12N 5/00 | (2006.01) |
| C12N 5/079 | (2010.01) |
| A61B 5/0432 | (2006.01) |
| A61K 48/00 | (2006.01) |
| A01N 63/00 | (2006.01) |
| A61K 35/54 | (2006.01) |
| A61N 1/32 | (2006.01) |
| A61K 38/19 | (2006.01) |
| A61N 1/36 | (2006.01) |

(52) U.S. Cl.

CPC ............... *A61K 38/18* (2013.01); *A61K 35/545* (2013.01); *A61N 1/326* (2013.01); *A61K 38/185* (2013.01); *A61K 38/19* (2013.01); *A61N 1/36082* (2013.01)

USPC ............... 514/1.1; 514/1.2; 514/1.3; 514/7.6; 514/8.3; 514/8.4; 600/378; 600/372; 600/373; 435/368; 424/93.1; 424/93.21

(58) Field of Classification Search

None

See application file for complete search history.

(56) References Cited

U.S. PATENT DOCUMENTS

| 5,119,832 A | 6/1992 | Xavier |
| 5,423,877 A | 6/1995 | Mackey |
| 5,458,631 A | 10/1995 | Xavier |
| 6,015,572 A | 1/2000 | Lin |
| 6,042,579 A | 3/2000 | Elsberry |
| 6,066,163 A | 5/2000 | John |
| 6,214,334 B1 | 4/2001 | Lee |
| 6,348,050 B1 | 2/2002 | Hartlaub |
| 6,650,943 B1 | 11/2003 | Whitehurst |
| 8,093,205 B2 * | 1/2012 | Shafer ............................ 514/1.1 |
| 2002/0019330 A1 | 2/2002 | Murray |
| 2002/0042597 A1 | 4/2002 | Hartlaub |
| 2002/0164791 A1 | 11/2002 | Van Der Kooy |
| 2002/0193301 A1 | 12/2002 | Twardzik |
| 2003/0036193 A1 | 2/2003 | Fallon |
| 2003/0088274 A1 | 5/2003 | Gliner |
| 2005/0123526 A1 | 6/2005 | Shafer |

FOREIGN PATENT DOCUMENTS

| WO | WO 95/13364 | 5/1995 |
| WO | WO 96/33731 | 10/1996 |
| WO | WO 01/12236 | 2/2001 |
| WO | WO 01/62336 | 8/2001 |
| WO | WO 02/083877 | 10/2002 |
| WO | WO 02/088330 | 11/2002 |
| WO | WO 02/094997 | 11/2002 |

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
Grill, Emerging Clinical Applications of Electrical Stimulation . . . , J. of Rehabilitation Research & Development, Nov./Dec. 2001, 641-653, vol. 38(6).
Deisseroth, Excitation-Neurogenesis Coupling in Adult Neural Stem/Progenitor Cells, Neuron, May 2004, 535-553, vol. 42.
Salimi, Rescuing Transient Corticospinal Terminations and Promoting Growth with Corticospinal Stimulation in Kittens, J. of Neuroscience, May 2004, 4952-4961, vol. 24(21).
Fallon, In Vivo Induction of Massive Proliferation, Directed Migration & Differentiation of Neural Cells in the Adult Mammalian Brain, PNAS, Dec. 19, 2000, 14685-14691, vol. 97(26).
White, Neural Crest Stem Cells Undergo Cell-Intrinisic Developmental Changes in Sensivitity to Instructive Diferentation Signals, Neuron, Jan. 2001, 57-71, vol. 29.
Lee, A Local Wnt-3a Signal is Required for Development of the Mammalian Hippocampus, Development 127, Jan. 2000, 457-467.

(Continued)

*Primary Examiner* — Chang-Yu Wang

(57) ABSTRACT

Devices and methods for treating diseases associated with loss of neuronal function are described. The methods are designed to promote proliferation, differentiation, migration, or integration of endogenous progenitor stem cells of the central nervous system (CNS). A therapy, such as an electrical signal or a stem cell enhancing agent, or a combination of therapies, is applied to a CNS region containing endogenous stem cells or a CNS region where the endogenous stem cells are predicted to migrate and eventually reside, or a combination thereof.

20 Claims, 19 Drawing Sheets

(56) References Cited

OTHER PUBLICATIONS

Nerlov, PU.1 Induces Myeloid Lineage Commitment in Multipotent Hematopoietic Progenitors, Genes & Development, 1998, 2403-2412, vol. 12.

Shah, Alternative Neural Crest Cell Fates are Instructively Promoted by TGFb Superfamily Members, Cell, May 1996, 331-343, vol. 85.

Martens, In Vivo Infusions of Exogenous Growth Factors into the Fourth Ventricle . . . , European J of Neuroscience, 2002, 1045-1057, vol. 16.

Newton, Gene Profile of Electroconvulsive Seizures . . . , J. of Neurosciene, Nov. 2003, 10841-10851, vol. 23(24).

Angelucci, Electroconvulsive Stimuli Alter the Regional Concentrations of Nerve Growth Factor . . . , J. of ECT, 2002, 138-143, vol. 18(3).

Mie, Induction of Neural Differentation by Electrically Stimulated Gene Expression of NeuroD2, J of Biotechnology, 2003, 231-238, vol. 100.

Yanagida, Electrically Stimulated Induction of hsp70 Gene Expression in Mouse Astroglia and Fibroblast Cells, J of Biotechnology, 2000, 53-61, vol. 79.

Kimura, Gene Expression in the Electrically Stimulated Differentation of PC12 Cells, J of Biotechnology, 1998, 55-65, vol. 63.

Jankowsky, Cytokine Respones to LTP Induction in the Rat Hippocampus: A Comparison of In Vitro and In Vivo Techniques, Learning & Memory, 2000, 400-412, vol. 7.

Okada, The Long-Term High-Frequency Repetitive Tarnscranial Magnetic Stimulation Does Not Induce mRNA . . . Brain Research 2002, 37-41, vol. 957.

Lukasiuk, cDNA Profiling of Epileptogenesis in the Rat Brain, European J of Neuroscience, 2003, 271-279, vol. 17.

Tian, Frequency-Dependent Expression of Cortioctropin Releasing Factor in the Rat's Cerebellum, Neuroscience, 2001, 363-377, vol. 121.

Schuldiner, Effects of Eight Growth Factors on the Differentiation of Cells Derived from Human Embryonic Stem Cells, PNAS, Oct. 2001, 11307-11312, Vo. 97(21).

Nerlov, Distinct C/EBP Functions are Required for Eosinophil Lineage Commitment and Maturation, 1998, Genes & Dev., 2413-2423, vol. 12.

Schmidt, Annu Rev. Biomed. Eng. 2003, 5:293-347.

Hoke, Nat. Clin. Pract. Neurol. 2006:448-454.

Wiessner, J. Cereb. Blood Flow Metab. Feb. 23, 2003: 154-165.

Doetsch, Curr. Opin. Genet. Dev. 2003. 13:543-550.

Doetsch, Cell 1999. 97:703-716.

't Hart Curr. Opin. Neurol. 2003 16: 375-383.

Blight Nat. Neurosci. 2002 5:1051-4, p. 316.

\* cited by examiner

METHOD FOR TREATING DAMAGED TISSUE OF THE CNS

RELATED APPLICATIONS

This application is a divisional application of U.S. application Ser. No. 11/000,856 filed Dec. 1, 2004, now issued as U.S. Pat. No. 8,093,205, which claims the benefit of priority from provisional applications Ser. Nos. 60/526,405 and 60/526,318, both filed on Dec. 1, 2003, of which are incorporated by reference herein in their respective entireties.

BACKGROUND

Over the past two decades, the concept of neurological tissue grafting or exogenous stem cell transplantation has been investigated for its potential to treat neurodegenerative disease such as Parkinson's disease. While such transplantation approaches represent a potential for a significant improvement over currently available treatments for neurological disorders, there are significant drawbacks to cell transplantation. First, ethical considerations make it difficult to obtain, enough cells with the desired characteristics to implement practical therapies. Upon transplantation the majority of cell types fail to integrate with host tissue making it necessary to implant high numbers of cells to boost the chances of integration. Furthermore, there is the chance that the implanted cells will be immunologically incompatibility with the host, the transplanted cells may result in tumor formation or pass infectious agents from the donor tissue to the host.

The presence of ongoing neurogenesis in the adult mammalian brain raises the exciting possibility that endogenous progenitor cells may be able to generate new neurons to replace cells lost through brain injury or neurodegenerative disease. Several researchers have demonstrated increased cell proliferation and the generation of new neurons in various diseased brains. Such findings have lead to the conclusion that mitotic activity persists in various regions of the adult mammal CNS.

Adult endogenous stem cells are activated in response to various injuries but their capacities to proliferate, migrate, differentiate to the appropriate cell type, make the appropriate contacts and perform the appropriate function (ie neurotransmitter release) is quite variable. This variability depends, in part on the lesion-type and the germinative zone from which they arise. Various works suggest that the ability of endogenous stem cells to proliferate, migrate, differentiate and integrate can be enhanced by various stimulation signals. For example, administration of growth factors and electrical stimulation have each been suggested to promote neurogenesis and conceivably direct the proliferation, migration, differentiation and integration of new cells in the central nervous system. However, the method of combining several different approaches simultaneously or in sequence, and device(s) to achieve this has not been previously disclosed.

Deep brain electrical stimulation (DBS) has been used as therapy for Parkinson's and other disorders of the CNS including pain. Although the mechanism of action is unknown, it is believed that DBS normalizes aberrant neuronal cell activity. However, there is some evidence to suggest that applying direct current electric fields can enhance the axonal growth of a neuron (summarized in Grill et al, 2001). More recently, two studies demonstrate that electrical activity can control the genesis of new neurons from stem cells and control the patterns of gowth of neurons extending from the cortex to the spinal cord (Deisseroth et al., 2004 and Salimi and Martin, 2004).

Others suggest that infusions of exogenous growth factors into the ventricles increase the proliferation of neural progenitors around the ventricle and the central canal of the spinal cord (Martens et al., 2002). Furthermore, Fallon et al (2000) describe the infusion of a growth factor to the caudate-putamen. The infusion of transforming growth factor alpha (TGFα) resulted in the proliferation, migration and integration of stem cells in to the substantia nigra of a 6-OHDA lesioned rats (Fallon 2000). Growth factors are one example of a soluble stimulation signal for neurogenesis. It is likely that a combination of extracellular signals and microenvironmental conditions may be necessary for the proliferation, differentiation, migration and integration of stem cells.

Methods such as transcranial magnetic stimulation (TMS), direct and indirect electrical stimulation have been proposed to treat a variety of disorders and conditions. The use of electrical stimulation in these methods is to drive the existing neurons for enhanced function.

Cell replacement therapy is another method for restoring functionality lost to several systems of the body due to damage, disease and or disorders of the central nervous system. Dead or dysfunctional cells in the brain or spinal cord are replaced by undifferentiated cells, such as stem cells or blast cells. These cells may be derived from cultured cells, dedifferentiated cell lines, cancer cell lines, fetal tissues or other progenitor cell types. These relatively undifferentiated cells transform themselves to replace and assume the duties of native cells lost due to disease, damage, or trauma. Accordingly, the implanted cells can assume many characteristics of the native cells that they are replacing. One method of cell replacement therapy (disclosed in U.S. Pat. No. 6,214,334 to Lee) is to implant mature neurons at the site of nerve damage. The mature neurons can develop as replacement cells for the destroyed or damaged neurons and can make necessary linkages to restore the functionality of the damaged neurons. However, the process of cell replacement therapy does not always result in full or even partial functionality of the replacement cells.

A method of cell replacement currently available for promoting recovery from damage to the CNS involves implanting stem cells within the brain or spinal cord and administering a neuronal stimulant to the cells as described in WO01/12236 to Finklestein et al. Finklestein discloses administering stem cells and neural stimulant in vivo to improve sensory, motor or cognitive abilities. In one embodiment, Finklestein discloses TMS as a neural stimulant. In another embodiment, the neural stimulant is an anti-depressant or combinations thereof. Finklestein does not mention the use of; or the administration of, growth factors, chemo attractant factors or other stem cell enhancing agents. Furthermore, Finklestein does not describe the promotion of endogenous cells for these purposes or with these stimulants.

WO96/33731 and others in its class disclose the administration of growth factors to promote the structural and functional integration of implanted, exogenous neurons or grafted tissue. Here the neurotrophic factor is administered to the CNS when the implanted neurons are optimally responsive to the factor. WO96/33731 does not describe the application of an electrical stimulation to promote the exogenous stem cells.

US2003/0088274 to Gliner et al describes electrically stimulating cells before and/or after being implanted in the nervous system of a patient to enhance the ability of cells to achieve increased functionality. In one aspect, Gliner describes electrically enhancing the achievement of full functionality of cells capable of differentiating into neurons implanted in a patient's nervous system. In another aspect, Gliner describes electrical stimulation of fully differentiated neurons implanted in patient's nervous system to promote growth and connectivity of the implanted neurons. Gliner describes applying the electrical stimulation to a defined portion of the brain where neural activity for carrying out the neural function actually occurs in the particular patient-usually the cortex. Gliner does not describe the use of electrical stimulation applied to endogenous (non-implanted) stem cell or stem cells-like populations of cell in the CNS to achieve similar functionality. Nor does Gliner describe the administration of growth factors, in addition to electrical stimulation to achieve functionality.

WO 95/13364 describes a method to treat a neurological disorder caused by lost or damaged neural cells. The invention discloses the method of administrating growth factors or genetic material to the ventricles. The administration of such agents is intended to promote the proliferation/differentiation and/or migration of the endogenous precursor cells lining the ventricle so as to replace the lost or damaged neural cells. While Wiess describes the promotion of endogenous stem cells for replacement therapy, the delivery of growth factors and genetic material is limited in delivery site (ventricles) and device (osmotic pump). Additionally, WO 95/13364 and others in its class do not disclose the use of electrical stimulation to promote the endogenous stem cells.

The aforementioned publications as well as other similar art discloses the application of soluble stem cell enhancing agents (such as growth factors) as well as electrical stimulation of stem cells to promote the proliferation, migration and integration of implanted, exogenous stem cells. However, none of the prior art mentions the combination of the two such approaches in a step-wise or simultaneous manner. Further, none describe or suggest the application of electrical signals or soluble enhancing agents to more than one CNS region to encourage proliferation, differentiation, migration or integration of stem cells.

SUMMARY

Given the problems raised with exogenous stem cell implantation, the current invention pertains to an improved method to promote recovery or damaged CNS tissue by making use of the endogenous (not-implanted) stem cells populations. The current disclosure describes devices and methods of combining electrical and chemical therapies to optimize the proliferation, differentiation, migration, and integration of endogenous stem cells. In addition, this disclosure describes administration of stem cell enhancing agents or electrical signals at more than one location to enhance treatment of disorders associated with loss of neuronal function.

In an embodiment, the invention provides an implantable medical device. The device comprises a housing and a pulse generator and a pump disposed in the housing. The device further comprises a reservoir operably coupled to the pump. The reservoir contains one or more stem cell enhancing agents. The one or more stem cell enhancing agents promote one or more of proliferation, migration, differentiation, and integration of a stem cell. In an embodiment, the invention provides a system comprising the implantable medical device, a lead, and a catheter. The lead may be operably coupled with the pulse generator and the catheter may be operably coupled to the pump.

An embodiment of the invention provides a method for treating a disease associated with a loss of neuronal function in a subject in need thereof. The method comprises implanting a first therapy delivery element comprising a therapy delivery region in the subject, positioning the therapy delivery region of the first therapy delivery element in a first CNS region containing endogenous stem cells, implanting a second therapy delivery element comprising a therapy delivery region in the subject, positioning the therapy delivery region of the second therapy delivery element in a second CNS region where the endogenous stem cells are predicted to migrate and integrate, applying a first therapy to the first CNS region via the therapy delivery region of the first therapy delivery element, and applying a second therapy to the first CNS region via the therapy delivery region of the second therapy delivery element. The first therapy is configured to promote the endogenous stem cells to proliferate, migrate, or differentiate. The second therapy is configured to promote one or more of proliferation of the endogenous stem cells, migration of the endogenous stem cells to the second CNS region, differentiation of the endogenous stem cells, or integration of the endogenous stem cells in the second CNS region cells. The first therapy delivery element may be a catheter or a lead and the therapy delivery region of the first therapy element may be an infusion section or an electrode. The second therapy delivery element may be a catheter or a lead and the therapy delivery region of the second therapy delivery element may be an infusion section or an electrode. The first therapy and the second therapy may be the same or different.

In an embodiment, the invention provides a method for treating a disease associated with loss of neuronal function in a subject in need thereof. The method comprises applying a first therapy to a first CNS region containing endogenous stem cells, and applying a second therapy to a second CNS region where the endogenous stem cells are predicted to migrate and integrate. The first therapy is configured to promote one or more of proliferation, migration, or differentiation of the stem cells. The second therapy is configured to promote one or more of proliferation, migration, differentiation, or integration of the stem cells. The first therapy and the second therapy may be the same or different.

In an embodiment, the invention provides a method for treating a disease associated with a loss of neuronal function in a subject in need thereof. The method comprises implanting a lead comprising an electrode within the subject, positioning the electrode in a CNS region containing endogenous stem cells, implanting a catheter comprising an infusion section within the subject, positioning the electrode in the CNS region containing the endogenous stem cells, applying an electrical signal via the electrode to the CNS region containing the endogenous stem cells, and applying a stem cell enhancing agent via the infusion section to the CNS region containing the endogenous stem cells. The electrical signal and the stem cell enhancing agent are configured to promote one or more of proliferation of the endogenous stem cells, migration of the endogenous stem cells, or differentiation of the endogenous stem cells.

An embodiment of the invention provides a method for treating a disease associated with a loss of neuronal function. The method comprises applying an electrical signal to a CNS region containing endogenous stem cells, and applying a stem cell enhancing agent to the CNS region containing endogenous stem cells. The electrical signal and the stem cell enhancing agent are configured to promote proliferation, migration, or differentiation of the endogenous stem cells.

In an embodiment, the invention provides a method for treating a disease associated with a loss of neuronal function in a subject in need thereof. The method comprises implanting a lead comprising an electrode in the subject, positioning the electrode in a CNS region where endogenous stem cells are predicted to migrate and reside, implanting a catheter comprising an infusion section in the subject, positioning the infusion section in the CNS region where the endogenous stem cells are predicted to migrate and reside, applying an electrical signal to the CNS region where the endogenous stem cells are predicted to migrate and reside, and applying a stem cell enhancing agent to the CNS region where the endogenous stem cells are predicted to migrate and reside. The electrical signal and the stem cell enhancing agent are configured to promote one or more of proliferation of the endogenous stem cells, migration of the endogenous stem cells to the second CNS region, differentiation of the endogenous stem cells, or integration of the endogenous stem cells in the second CNS region.

In an embodiment, the invention provides a method for treating a disease associated with a loss of neuronal function in a subject in need thereof. The method comprises applying an electrical signal to a CNS region where endogenous stem cells are predicted to migrate and reside, and applying a stem cell enhancing agent to the CNS region where endogenous stem cells are predicted to migrate and reside. The electrical signal and the stem cell enhancing agent are configured to promote one or more of proliferation of the endogenous stem cells, migration of the endogenous stem cells to the CNS region, differentiation of the endogenous stem cells; or integration of the endogenous stem cells in the second CNS region.

One or more embodiments of the invention provide advantages over existing devices and methods for treating diseases associated with diminished neuronal function. For example, the use of soluble chemical agents and electrical signals together should prove more efficacious than either alone for treatment of diseases associated with loss of neuronal function. The combination of electrical signals and soluble chemical agents should enhance the proliferation, migration, differentiation, and integration of endogenous stem cells. The use of chemical agents or electrical signals at more than one location in the CNS may serve to ensure the endogenous stem cells proliferate sufficiently, migrate to the appropriate location, differentiate, and integrate into the appropriate location. The deficiencies of application of only electrical or only chemical therapies at only one location may be overcome using the description provided herein.

The drawings are not necessarily to scale.

DETAILED DESCRIPTION

In the following descriptions, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense.

Definitions

All scientific and technical terms used in this application have meanings commonly used in the art unless otherwise specified. The definitions provided herein are to facilitate understanding of certain terms used frequently herein and are not meant to limit the scope of the present disclosure.

As used herein, "subject" means a living being having a nervous system, to which living being a device or method of this disclosure is applied. "Subject" includes mammals such as mice, rats, pigs, cats, dogs, horses, non-human primates and humans.

As used herein, the terms "treat", "therapy", and the like are meant to include methods to alleviate, slow the progression, prevent, attenuate, or cure the treated disease.

As used herein, "disease associated with loss of neuronal function" means a disease, disorder, condition, and the like resulting from impairment of nervous tissue function. The impairment may result from damage to nervous tissue, such as a neuron or glial cell. Nervous tissue may be damaged genetically or through infection, disease, trauma, and the like. As used herein, "repairing damaged neural tissue" means improving, restoring, replacing the function of a damaged neuron. A neuron may be damaged genetically or through infection, disease, trauma, and the like.

As used herein, "promoting neurogenesis" refers to a series of events (including proliferation of a neural precursor or stem cell) that results in the appearance of a new neuron.

As used herein, "endogenous stem cell" means stem cells that are already present in the body. Endogenous stem cells include multipotent, totipotent, pluripotent stem cells that are present in an organ or tissue of a subject. Such cells are capable of giving rise to a fully differentiated or mature cell types.

Delivery of Therapy

Figure 17:
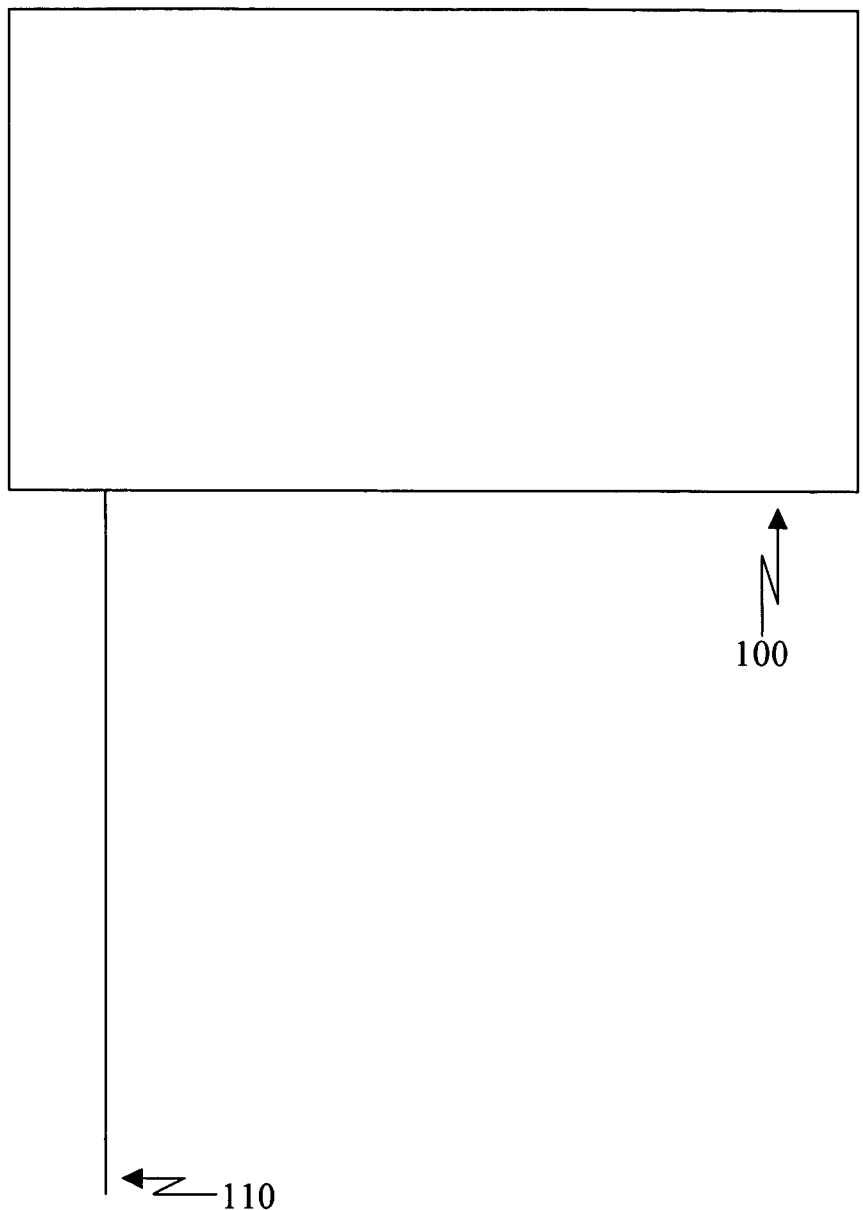
FIG. 17 is a drawing of a therapy delivery device coupled to a therapy delivery element.

Referring to FIG. 17, a therapy delivery device 100 may be operably coupled to therapy delivery element 110. A therapy delivery region (not shown) of therapy delivery element 110 may be positioned in a subject's central nervous system (CNS) to deliver a therapy. The therapy may be a therapeutic agent or an electrical signal. Therapy delivery element 110 may be a catheter or a lead, and therapy delivery region may be an infusion region of a catheter or an electrode.

Figure 1:
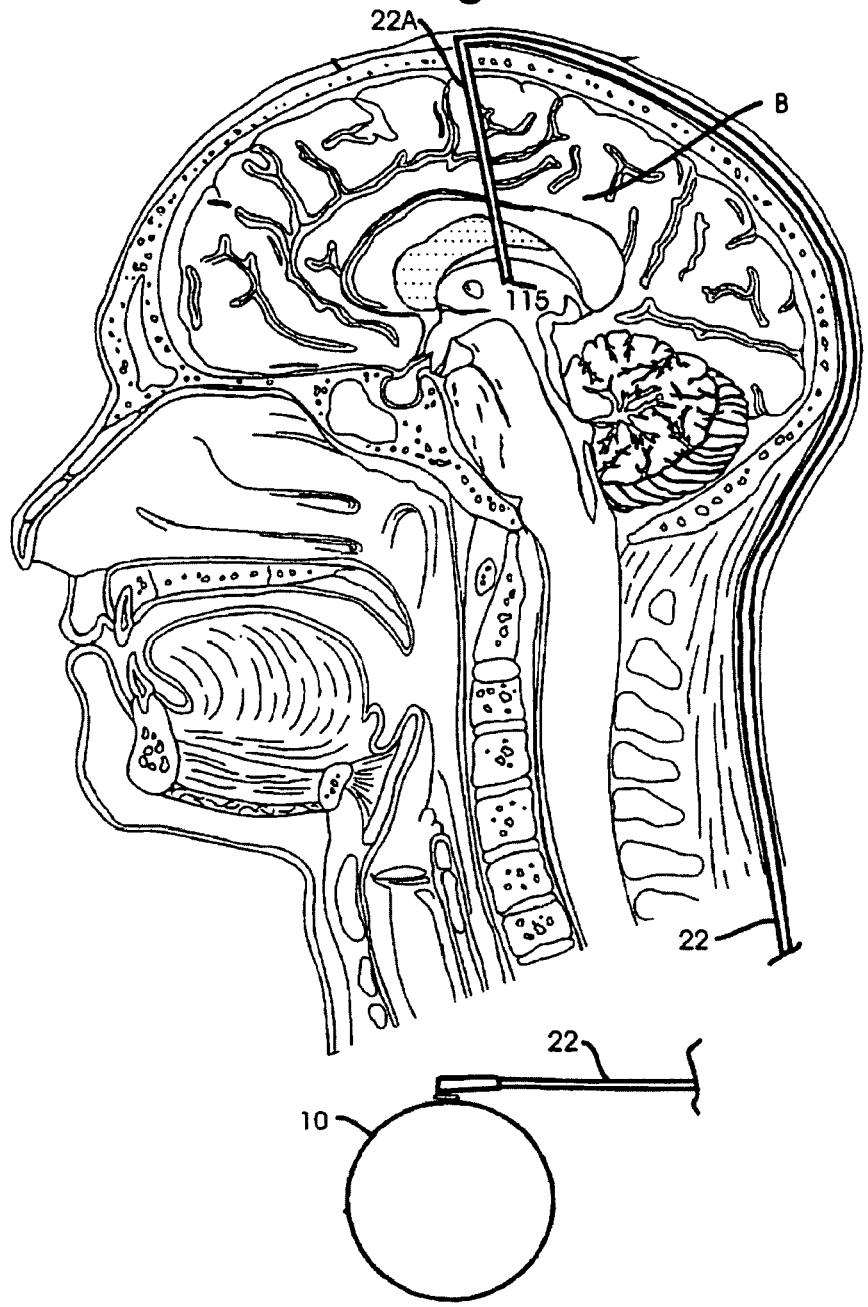
FIG. 1 is a drawing of a therapy delivery system adapted to deliver therapy to a subject's brain.

Referring to FIG. 1, a therapy delivery region 115 of a therapy delivery element 22 may be positioned to deliver therapy within a brain region of a subject. Therapy delivery region 115 is shown at distal portion of therapy delivery element 22, but it will be understood that therapy delivery region 115 may be located at any position along therapeutic element 22. The therapy delivery element 22 may be coupled to a therapy delivery device 10. The device 10 may be, e.g., a signal generator or a pump for delivering a therapeutic agent. The device 10 may be implantable. There may be more than one therapy delivery element 22 coupled to the device 10. An individual delivery element 22 may be divided into two portions 22A and 22B that may be implanted into the brain bilaterally. Alternatively, a second device 10 and therapeutic element may be used to deliver therapy to a corresponding brain region in a second brain hemisphere.

Figure 18:
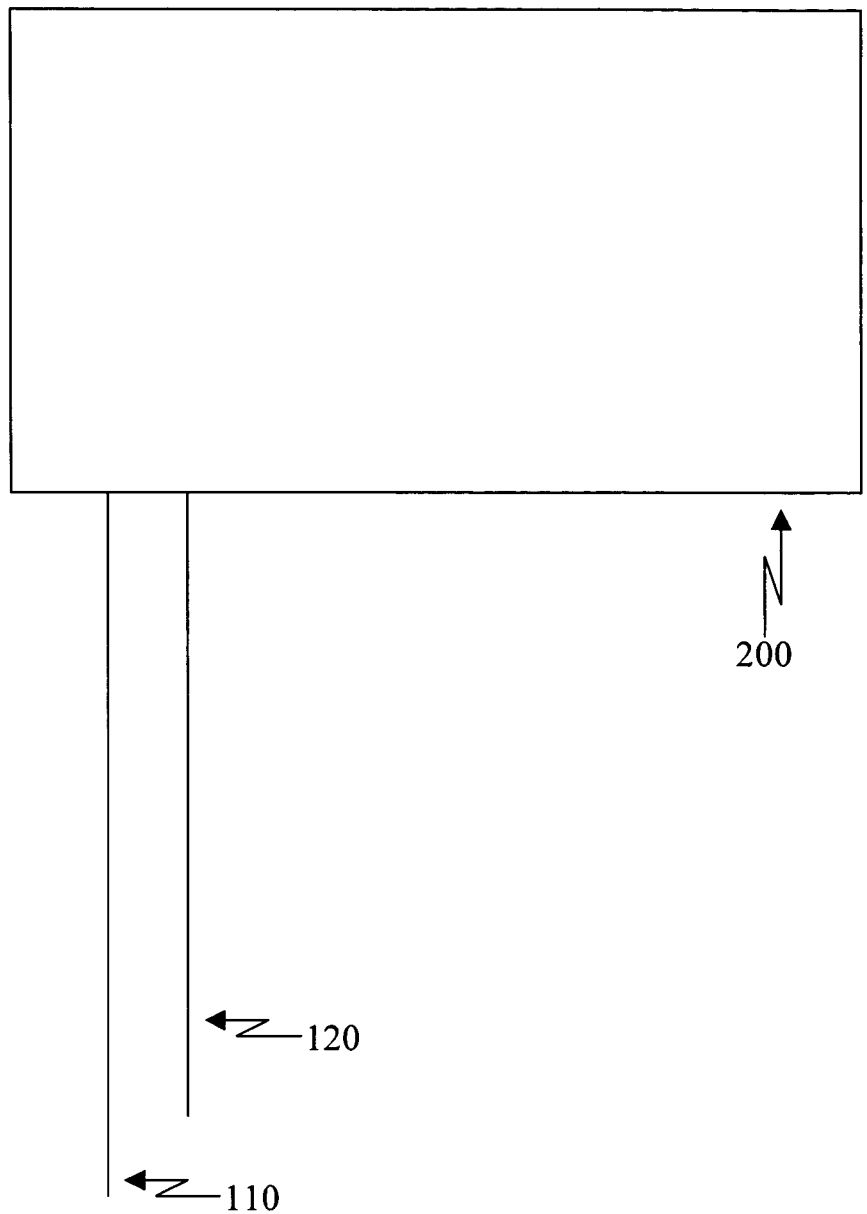
FIG. 18 is a drawing of a therapy delivery device coupled to two therapy delivery elements.
Figure 19:
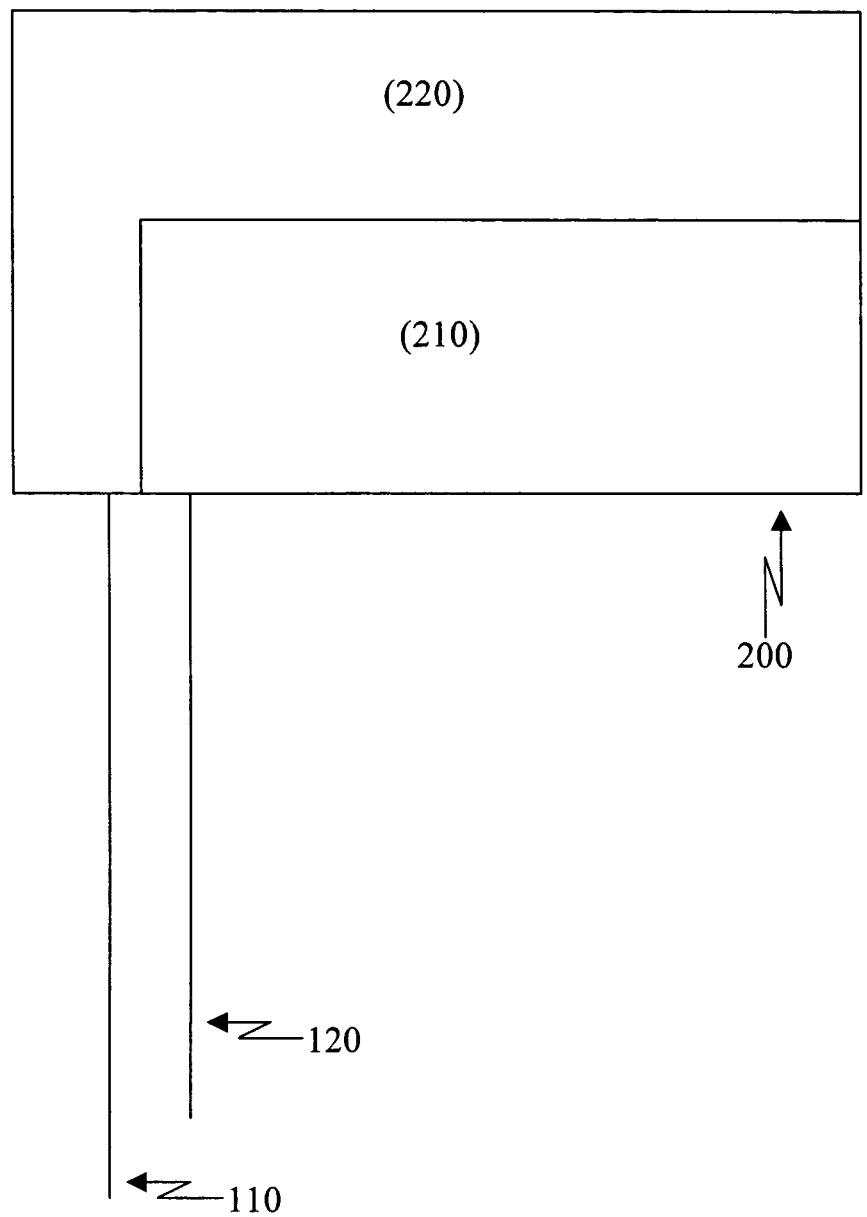
FIG. 19 is a drawing of a therapy delivery device having two therapy delivery units, each coupled to a therapy delivery element.

Referring to FIG. 18, therapy delivery device 200,100 operably coupable to two therapy delivery elements 110, 120, 22 is shown. It will be understood that therapy delivery device 200,100 may be coupled to more than two therapy delivery elements 110, 120, 22. As shown in FIG. 19, therapy delivery device 200,100 may have two therapy delivery units 210, 220, which may be the same or different. For example, therapy delivery units 210, 220 may both comprise electrical signal generators, may both comprise pump mechanisms, or one may comprise a signal generator and one may comprise a pump mechanism. Devices 200, 100 comprising a combination of a electrical signal generator and an a pumping mechanism may take the form of a device described in, e.g., U.S. Pat. Nos. 5,119,832, 5,423,877 or 5,458,631, each of which are hereby incorporated herein by reference in their entireties. It will be understood that device 200, 100 may have more than two delivery units 210, 220.

Figure 2:
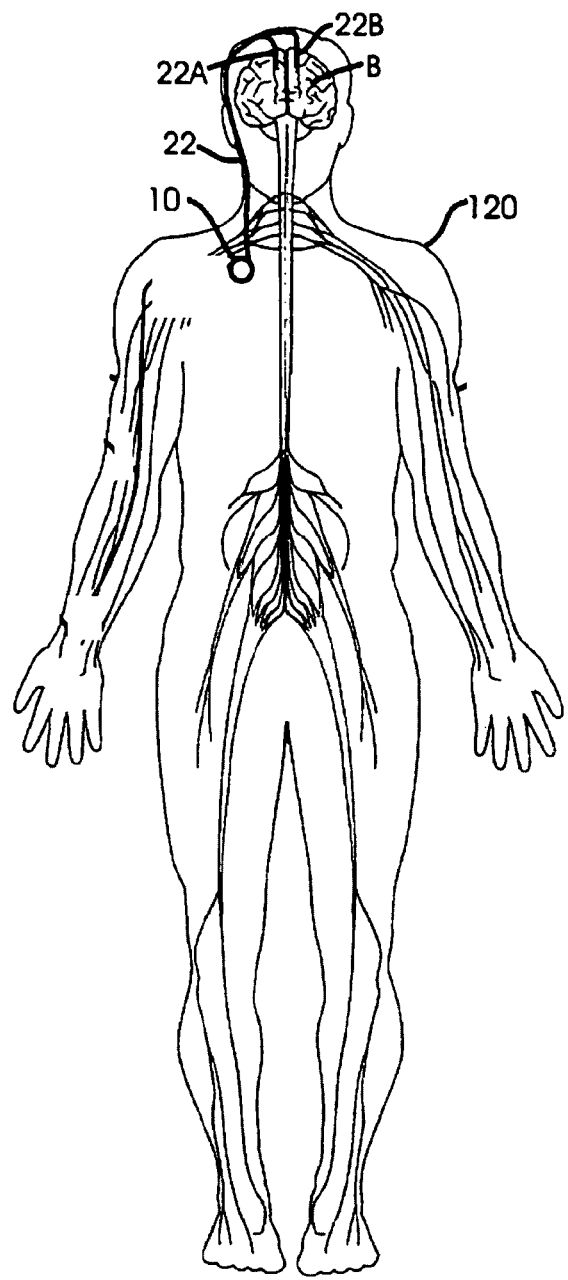
FIG. 2 is a drawing of an implantable therapy delivery system adapted to deliver therapy to a subject's brain.

Referring to FIG. 2, device 200, 100, 10 may be implanted in a human body 120. The device 200, 100, 10 may be implanted in the location shown or any other location suitable for the coupled therapeutic element 120, 110, 22 to deliver therapy to a region of the brain. Such other suitable locations include the abdomen, the cranium, and the neck. Therapy delivery element 120, 110, 22 may be divided into twin portions 22A and 22B that are implanted into the brain bilaterally. Alternatively, portion 22B may be supplied with therapy from a separate element 120, 110, 22) and device 200, 100, 10.

Electrical Signal

In an embodiment of the invention, an electrical signal is applied to a region of a subject's CNS. The CNS region may be, e.g., a brain region having an endogenous source of neural progenitor stem cells, a brain region to which endogenous stem cells are predicted to migrate or integrate, a brain region to which differentiated stem cell neurons are predicted to send projections, and the like. An "electrical signal" refers to an electrical or electromagnetic signal. In an embodiment, the signal has a pulse width, a frequency, an amplitude, a polarization, and a duration. An electrical signal may be depolarizing, may be hyperpolarizing, may increase the likelihood that a neuron will undergo an action potential, or may decrease the likelihood that a neuron will undergo an action potential. An electrical signal may be produced by any means suitable for application of the signal to a region of the subject's CNS. In an embodiment, the electrical signal is generated by a pulse generator. The pulse generator may be implantable.

Figure 3:
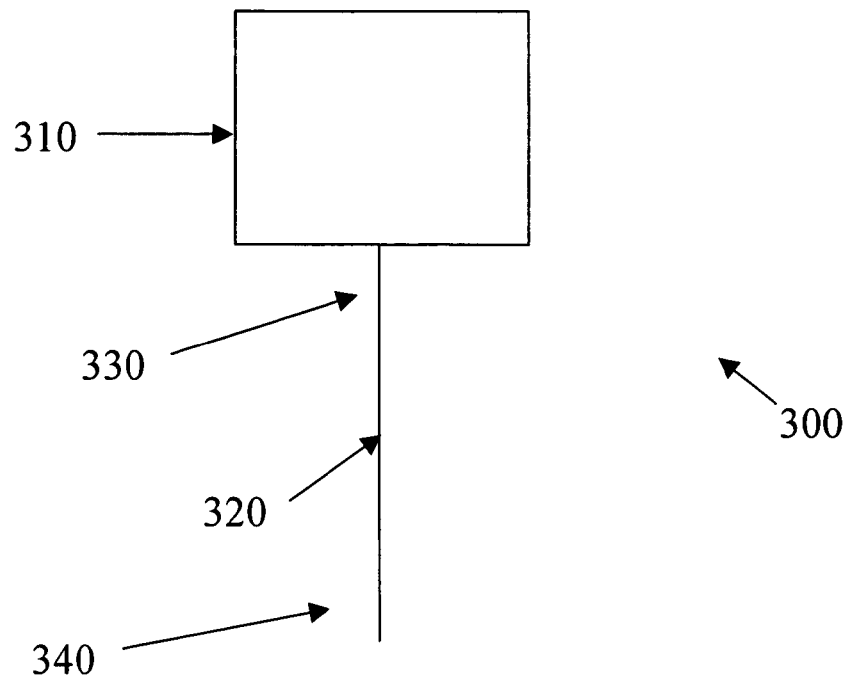
FIG. 3 is a drawing of a pulse generator therapy system.
Figure 4:
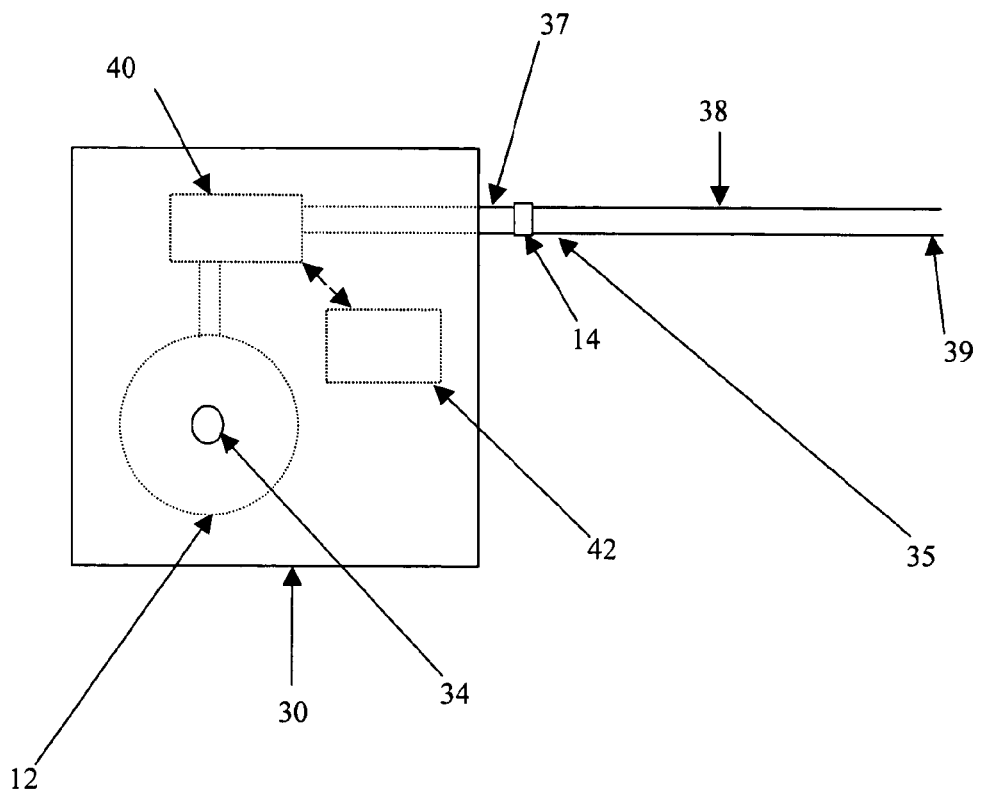
FIG. 4 is a drawing of a pump system for delivering a therapeutic agent.

Referring to FIG. 3, a pulse generator system 300 includes a pulse generator 310 and one or more leads 320. Any suitable pulse generator 310 and lead 320 may be used in accordance with various embodiments of the invention. A suitable pulse generator 310 includes Medtronic Model 3625 test stimulator. A suitable lead 320 includes any of the Medtronic leads sold with the Model 3625, such as Model YY0050931R or other custom made leads. Lead 320 is electrically coupled to pulse generator 310. A proximal portion 330 of the lead 320 is coupled to the pulse generator. A distal portion 340 of the lead 320 may be positioned to apply an electrical signal produced by a pulse generator 310 to a brain region having an endogenous source of neural progenitor stem cells.

The pulse generator 310 may be implantable as shown for the device 10 in FIG. 2. An implantable pulse generator system 300 includes an implantable pulse generator 310, such as Medtronic's Model 7425 Itrel or Model 7427 Synergy. Typically, the implantable pulse generator 310 will be electrically coupled to one or more leads 320. Suitable leads 320 are known and can typically be purchased with implantable pulse generators 310. Examples of suitable leads 320 include Medtronic's Pisces leads, Resume leads and other custom builds. The one or more leads 320 may be positioned to apply an electrical signal produced by the implantable pulse generator 310 to a brain region having an endogenous source of neural progenitor stem cells.

A pulse generator 310, whether or not it is implantable, may be programmed to adjust electrical signal parameters such as pulse width, frequency, amplitude, polarization, and duration. A physician or other person skilled in the biomedical arts with respect to neurostimulation will understand that the parameters may be optimized to achieve an electrical signal having desired properties. The parameters and the location of the application of the electrical signal may be varied to optimize therapeutic effect. In an embodiment, an electrical signal having a voltage of between about 1 mV to about 10 mV, a frequency of about 1 Hz to about 1000 Hz, and a pulse width of about 1 μsec to about 500 μsec is applied to a CNS region to promote the proliferation, differentiation, migration or integration of a stem cell.

Delivery of Therapeutic Agent

In an embodiment of the invention, one or more stem cell enhancing agents may be administered to a CNS region of a subject. The CNS region may be, e.g., a brain region having an endogenous source of neural progenitor stem cells, a brain region to which endogenous stem cells are predicted to migrate or integrate, a brain region to which differentiated stem cell neurons are predicted to send projections, and the like. It will be understood that therapeutic agents in addition to stem cell enhancing agents may also be administered. The additional therapeutic agents may be beneficial for treating a disease associated with loss of neuronal function.

Referring to FIG. 2, a system for delivering a therapeutic agent to a brain region of a subject is shown. The device 20 comprises a pump 40, a reservoir 12 for housing a composition comprising a therapeutic agent, such as a growth factor, and a catheter 38 having a proximal portion 35 operably coupled to the pump 40 and an infusion section 39 adapted for infusing the composition to the brain region of the subject. The device 20 may be an implantable pump, as shown regarding the device 10 in FIG. 2, or may be an external pump. The device 20 may have a port 34 into which a hypodermic needle can be inserted to inject a quantity of therapeutic agent into reservoir 12. The device 20 may have a catheter port 37, to which the proximal portion 35 of catheter 38 may be coupled. The catheter port 37 may be operably coupled to reservoir 12. A connector 14 may be used to couple the catheter 38 to the catheter port 37 of the device 20. The device 20 may contain a microprocessor 42 or similar device that can be programmed to control the amount of fluid delivery. The device may take the form of Medtronic's SynchroMed EL or SynchroMed II infusion pump system.

It will be understood that a therapeutic agent may be administered to a brain region without use of a pump system 20.

Stem Cell Enhancing Agent

In an embodiment of the invention, one or more stem cell enhancing agent may be administered in addition to a stimulation signal. As used herein, a "stem cell enhancing agent" is an agent that alone or in combination with another stem cell enhancing agent or an electrical signal increases the likelihood that a progenitor stem cell will migrate, proliferate, differentiate, integrate or release a factor that may result in a neural cell migrating, proliferating, differentiating, or integrating. Stem cell enhancing agents are chemical compounds and may be small molecule chemical agents; nucleic acids; including vectors, small inhibitory RNA, ribozymes, and antisense molecules; polypeptides, and the like. While some stem cell enhancing agents may affect the ability of a cell to selectively proliferate, differentiate, migrate, or integrate, it will be understood that many stem cell enhancing agents will affect the ability of a cell to undergo a combination of more than one of proliferate, differentiate, migrate and integrate. Accordingly, a discussion of a stem cell enhancing agent as an agent that, e.g., promotes proliferation does not necessarily indicate that the agent may not also promote one or more of differentiation, migration, and integration. It will also be understood that a stem cell enhancing agent may differentially affect proliferation, differentiation, migration, and integration based upon the location in which the agent is administered.

A stem cell enhancing agent may be a growth factor. Any growth factor capable of repairing damaged neural tissue and/or promoting neurogenesis may be administered. Exemplary suitable growth factors include glial-derived neurotrophic factor (GDNF), brain-derived neurotrophic factor (BDNF), fibroblast growth factor (FGF), vascular endothelial growth factor (VEGF), nerve growth factor (NGF), neurotrophin (NT), transforming growth factor (TGF), ciliary neurotrophic factor (CNTF), epidermal growth factor (EGF), insulin-like growth factor (IGF), stromal cell factor (SCF), notch, heparan sulfate proteoglycans (HSPGs) and growth factors within these classes such as, for example, NT-3, IGF-1, FGF-2, SCF-1 and TGF-alpha. More than one growth factor may be administered. Each growth factor may be administered in the same brain region or may be administered in different locations. Any amount of a growth factor may be administered. Preferably, an amount of a growth factor capable of promoting stem cell proliferation, differentiation, migration, or integration, when administered alone or in combination with stimulation and/or additional therapeutic agents, is administered. It will be understood that that the efficacy of a growth factor may be enhanced by a cofactor. For example, administration of cofactor cystatin C and IGF may enhance the efficacy of FGF-2. In an embodiment of the invention, daily doses of growth factors administered are in the range of about 0.5 micrograms to about 100 micrograms. For specific daily dose ranges for NGF, BDNF, NT-3, CNTF, IGF-1, and GDNF that may be administered, see U.S. Pat. No. 6,042,579, which is incorporated herein by reference in its entirety.

Any growth factor may be administered. Some growth factors may be referred to in the art as mitogens. In addition to the growth factors listed above, other mitogens suitable for use in accordance with the teachings of this disclosure include bone morphogenic proteins (BMP), noggin, erythropoietin, and leukemia inhibitory factor (LIF).

A growth factor or other stem cell enhancing agent may be a chemoattractant agent. A chemoattractant agent is an agent that directs a migrating cell to a particular region or an agent that directs neuronal projections to a particular agent. Examples of chemoattractant agents include stromal-cell-derived factor (SCF-1), fractalkine, growth related oncogene alpha (GRO-α), IL-8, MIP-1a, MIP-1b, MCP-1, MCP-2, MCP-3, GRO-a, GRO-b, GRO-g, RANTES, and eotaxin A stem cell enhancing agent may be an agent that inhibits factors that prevent extensive cell replacement. Such agents include an anti-nogo antibody, a p75ntr antagonist, a Rho-kinase inhibitor, and a nogo-66 receptor antagonist.

A stem cell enhancing agent may include agents that increase the likelihood that a neuron will undergo an action potential. Such agents include glutamate receptor agonists, such as LY 354740 or 5-dihydroxyphenylglycine (DHPG) and GABA receptor antagonists, such as CGP56433A or bicuculline.

Other neurotransmitters and agonists of their receptors that may be useful for promoting the proliferation, differentiation, migration, or integration of a stem cell include norepinepherine, acetylcholine, dopamine, serotonin, and the like.

Endogenous Source of Progenitor Stem Cells

In an embodiment of the invention, an electrical signal, a stem cell enhancing agent, or a combination thereof is applied to a region of the CNS having an endogenous source of progenitor stem cells. Therapy, whether electrical or chemical, may be applied to any CNS region having an endogenous source of progenitor stem cells. Such regions include, for example, a subventricular zone, basal ganglia, and dentate gyms. A subventricular zone includes a mediolateral wall of a lateral ventricle. Dentate gyms includes hippocampus and subregions thereof. Basal ganglia includes putamen, caudate nucleus, globus pallidus, subthalamic nucleus, and substantia nigra. Specific germinative areas of endogenous stem cells include the granule cell layer of the dentate gyms in the hippocampus and the olfactory bulb. More specifically, new neurons are generated respectively, from the subgranular zone of the dentate gyms and the subventricular zone of the lateral ventricles. Other target stem cell populations as suggested in the literature may include but are not limited to the: the cortex, the fourth ventricle and the central canal of the spinal cord, the ependymal later, hippocampus, striatum, septum, thalamus, hypothalamus, cerebral cortex, cerebellum, retina, medial gagnlionic eminence, optic nerve and spinal cord.

Brain Region with Damaged Tissue

In an embodiment of the invention, an electrical signal or a stem cell enhancing agent may be applied to a region of a brain having damaged neural tissue or damage to the glial cells. An electrical stimulation signal or a stem cell enhancing agent may be applied to any brain area having damaged neural tissue. In an embodiment, a therapy (i.e, electrical signal, stem cell enhancing agent, or combination thereof) is applied to a brain region having an endogenous source of progenitor stem cells and a brain region having damaged neural tissue.

Damaged neural tissue may arise from a genetic source, a disease, and/or a trauma. Damaged neural tissue may result from a neurodegenerative disease, such as Parkinson's disease and Alzheimer's disease. In Parkinson's disease, damage neural tissue May be found in the substantia nigra. In Alzheimer's disease, damaged neural tissue may be found in the basal forebrain, particularly the nucleus basalis of meynert, or the hippocampus, specifically the CA1 region. In a condition such as spinal cord injury, it may be desirable to administer a therapy to intrathecally at or near the level of the injury. Damaged neural tissue will be readily identifiable to a physician or other persons skilled in the biomedical arts.

Brain regions having damaged neural tissue may be the same or different from brain regions having an endogenous source of progenitor stem cells.

One exemplary therapy includes the administration of the growth factor, TGF-alpha, at a dose and rate sufficient to encourage proliferation, differentiation, migration, or integration. A suggested rate is in the range from about 0.2 µl/day to about 24 µl/day. A suggested dose is in the range from about 0.1 mg/ml to about 100 mg/ml.

Another exemplary therapy includes the administration of noggin and BMP. Temporally and spatially controlled administration of BMP and noggin may be achieved using a device (s) as described herein or as known in the art. Exogenous noggin may be delivered to the ependymal cells to promote neuronal differentiation whereas exogenous BMP may be delivered to the same area to promote glial differentiation.

Another exemplary therapy includes applying an electrical signal to promote the expression of an endogenous gene product at parameters sufficient to encourage the proliferation, differentiation, migration or integration of an endogenous stem cell. For example, the endogenous expression of c-fos, neuroD2, nogging, or various other stem cell enhancing agents may be encouraged. Electrical signal parameters may be in the range from, e.g., about 1 Hz to about 150 Hz, about 90 μsec to about 500 μsec, and about 0.1 V to about 10V.

In addition to delivering a stem cell enhancing agent to a CNS region comprising damaged neural tissue, it may be desirable to deliver such agents intraventricularly or intrathecally. Such non-targeted delivery of therapy may broadly encourage the proliferation or migration of stem cells.

Brain Regions to which Neurons Project

In an embodiment, therapy is delivered to a CNS region in which neurons are predicted to project. More particularly, therapy may be administered to a region where differentiated neuronal stem cells are expected to project to facilitate the newly developed or existing yet damaged neurons to make the appropriate neuronal connections.

Regions to which neurons are expected to send projections are known to those of skill in the art. For example, neurons of the substantial nigra send projections to the putamen. Accordingly to treat Parkinson's disease, it may be desirable to encourage newly integrated or differentiated neurons or damaged neurons of the substantia nigra to send projections to the putamen. This may be accomplished by delivering electrical signal, a stem cell enhancing agent, or a combination thereof to the putamen to encourage the neurons of the substantia nigra to make appropriate connections with neurons of the putamen.

In another example, a group of cholinergic neurons in the basal forebrain project to the neocortical and medial temporal regions. In Alzheimer's disease this group of cholinergic neurons are selectively damaged, resulting in severe impairment of learning. It may be desirable to encourage newly integrated or differentiated neurons of the basal forebrain to send projections to the neocortical and medial temporal regions. Furthermore, it may be desirable to encourage the newly established neuronal cell to produce acetylcholine to restore the function of the cholinergic transmission in the brain area. This may be accomplished by delivering electrical signal, a stem cell enhancing agent, or a combination thereof to the neocortcal and the medial temporal regions to encourage the neurons of the basal forebrain to make appropriate connections with neurons of the neocortical or medial temporal region. Likewise, replacement strategy may be achieved by delivering electrical signal, a stem cell enhancing agent, or a combination thereof to the basal forebrain to encourage the neurons of the neocortical and medial temporal regions to make appropriate connections with neurons of the basal forebrain.

Other neurotransmitter systems are selectively disrupted by the Alzheimer's disease process in a manner similar to the cholinergic system. In another example, the cortically projecting norepinephrine neurons of the locus coeruleus and the raphe neurons of the dorsal and central raphe nuclei are disrupted. It may be desirable to encourage newly differentiated or integrated or damaged neurons of the locus coeruleus and the raphe nucleus to send projections to the, cortex. This may be accomplished by delivering electrical signal, a stem cell enhancing agent, or a combination thereof to the locus coeruleus and the raphe nucleus.

In another example, axons of the neurons in the spinal cord may traverse some distance in the spinal cord on their way to project to a particular spinal cord level. During spinal cord injury, these axonal projections are damaged, resulting in impairment of sensory and movement functions and often paralysis. It may be desirable to encourage the newly integrated or differentiated neurons of one spinal cord level to send projections to the other spinal cord level in a manner that will result in an the repair of axonal projections over the injured area.

Therapy

In various embodiments of the invention, therapy may be delivered to one or more CNS regions to treat a disease associated with loss of neuronal function. One or more therapies, e.g. electrical signal and stem cell enhancing agent, may be delivered to, e.g., one or more of an endogenous source of progenitor stem cells, a region comprising damaged neuronal tissue, or a region to which neurons project. In various embodiments, a stem cell enhancing agent is delivered to two or more of such regions. In various embodiments, electrical signals and stem cell enhancing agents are delivered to one or more of such regions. For example a stimulation signal and a stem cell enhancing agent may be delivered to the same CNS region or may be delivered to different CNS regions.

An embodiment of the invention provides a method for treating a disease associated with loss of neuronal function, where therapy is directed to a brain region having an endogenous source of progenitor stem cells and a brain region having damaged neural tissue. Therapy may be application of an electrical signal or delivery of a stem cell enhancing agent. Therapy may be applied to any brain region having an endogenous source of progenitor stem cells and any brain region having damaged neural tissue.

Figure 5:
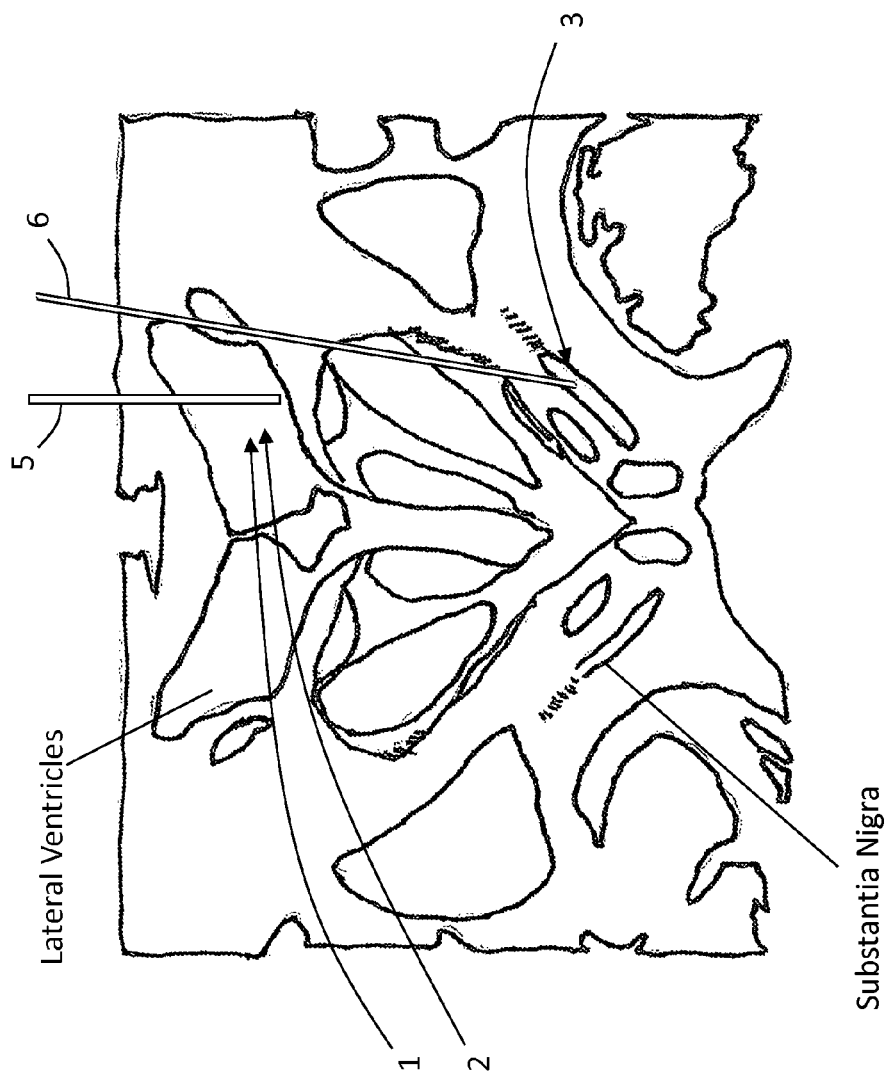
FIG. 5 is an illustration of therapeutic elements adapted to deliver therapy to two different brain regions, one region being a source of endogenous progenitor stem cells, the other representing a region having damaged neural tissue.

Referring to FIG. 5, an exemplary embodiment is shown where an electrical signal is applied and a stem cell enhancing agent is delivered. As shown in FIG. 5, a catheter with an electrode 5 may be positioned in a region containing endogenous stem cells. The catheter with an electrode 5 is positioned at the lateral walls of the ventricles. At step 1, a stem cell enhancing agent may be delivered via the catheter with the electrode 5 to the lateral walls of the ventricles. At step 2, an electrical signal may also be applied to the lateral walls of the ventricles. As shown in FIG. 5, a catheter 6 may be placed to deliver a stem cell enhancing agent at a location containing damaged nervous tissue. In the example provided by FIG. 5, the catheter 6 is positioned to deliver the stem cell enhancing agent to the substantia nigra. At step 3, a chemoattractant stem cell enhancing agent is delivered to the substantia nigra to draw stem cells to the targeted CNS region.

Figure 6:
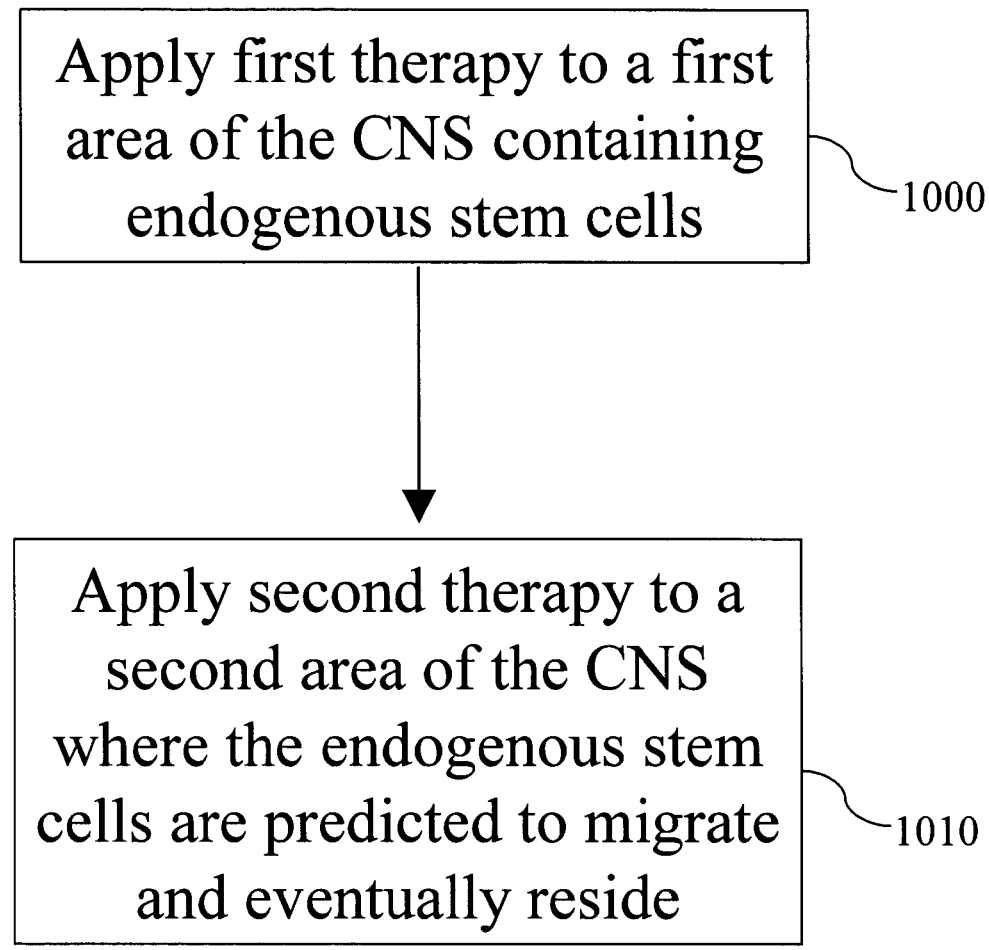
FIGS. 6-16 are flow charts illustrating various methods for treating a disease associated with loss of neuronal function.
Figure 7:
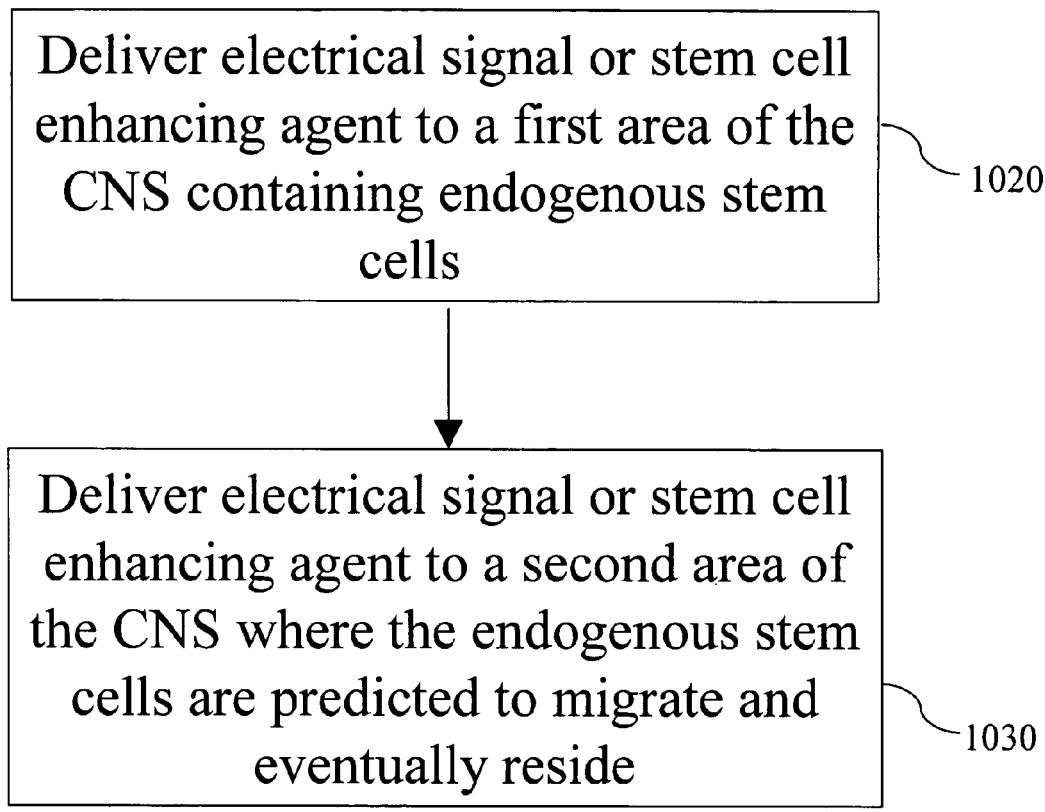

Referring to FIG. 6, an overview of a method of treating a disease associated with a loss of neuronal function is shown. As shown in FIG. 6, a first therapy may be delivered to a first area of the CNS containing endogenous stem cells (1000). As shown in FIG. 7 at 1020, the therapy may be an electrical signal or a stem cell enhancing agent. A second therapy is applied to a second area of the CNS where the endogenous stem cells are predicted to migrate and eventually reside (1010). As shown in FIG. 7 at 1030, the therapy may be an electrical signal or a stem cell enhancing agent. The first and second therapy may be the same or different.

Figure 8:
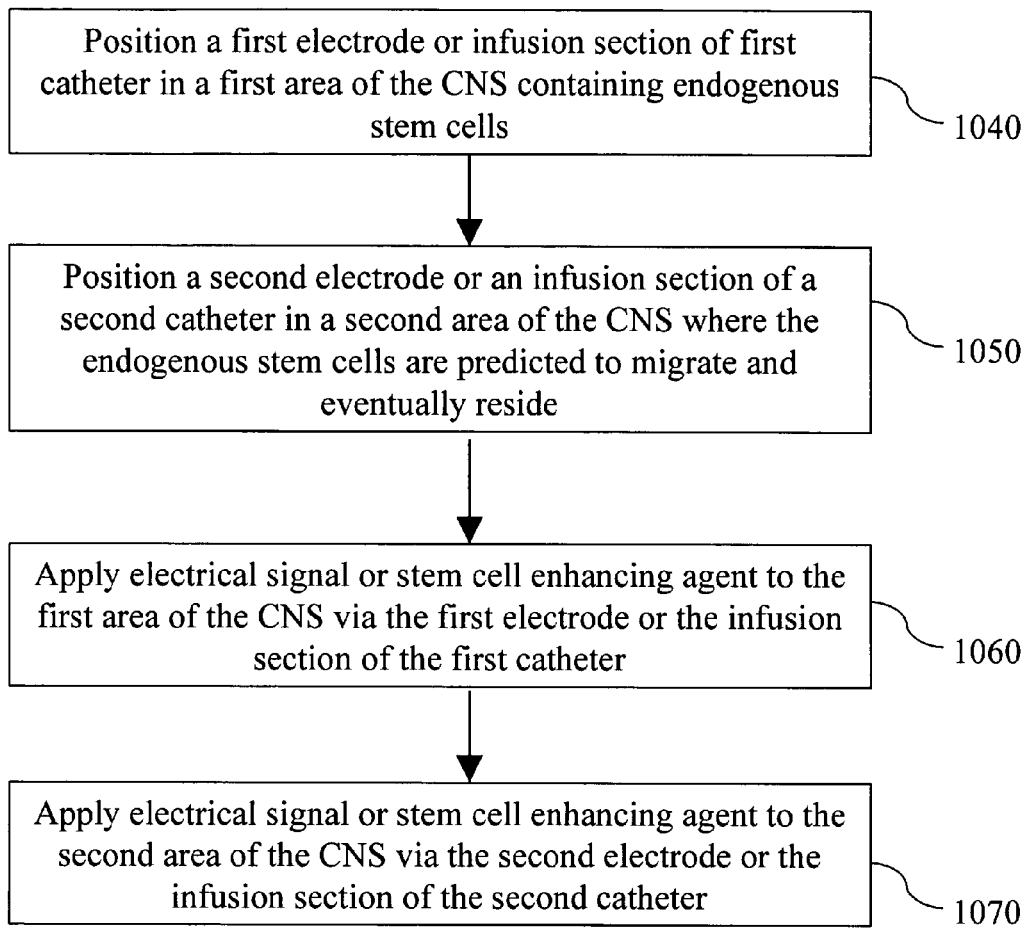
Figure 9:
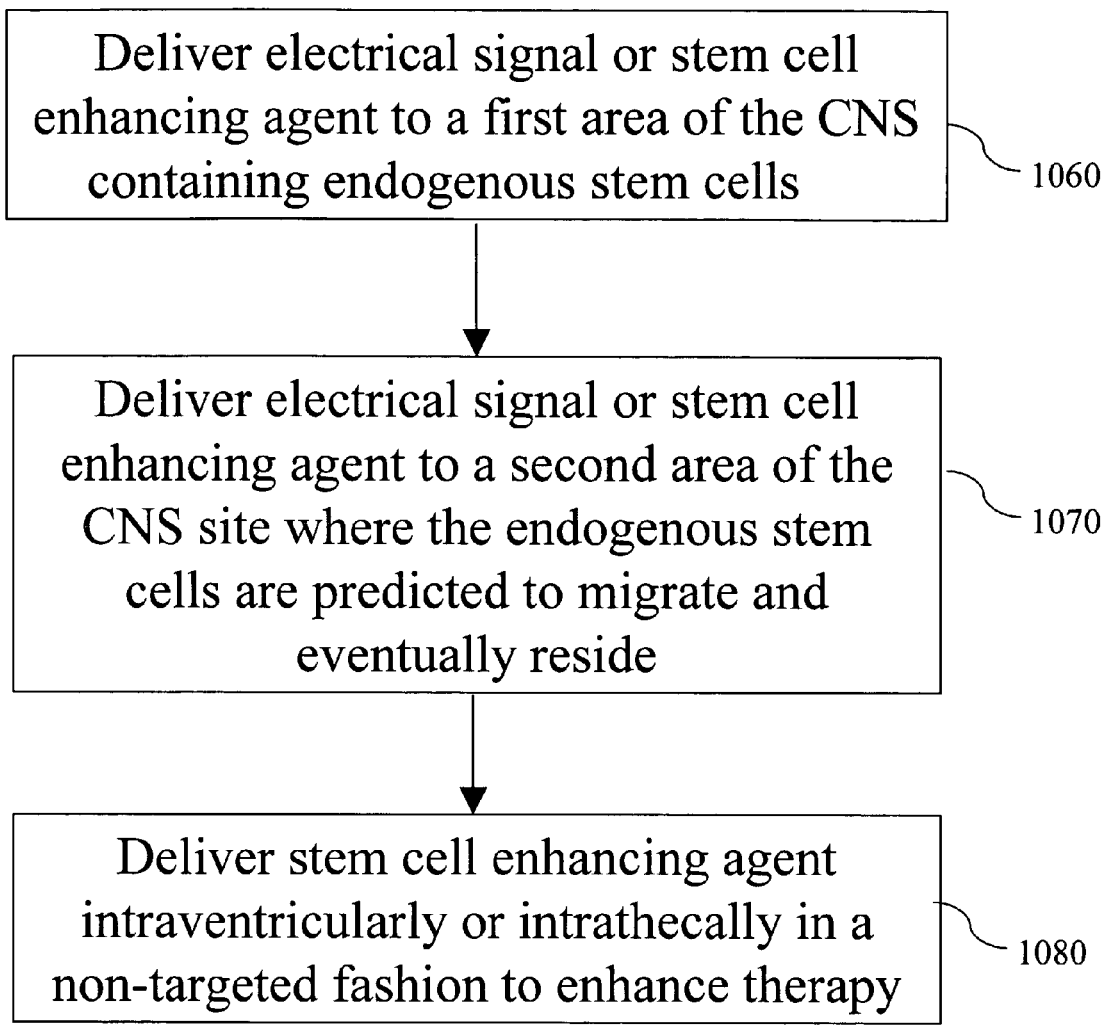
Figure 10:
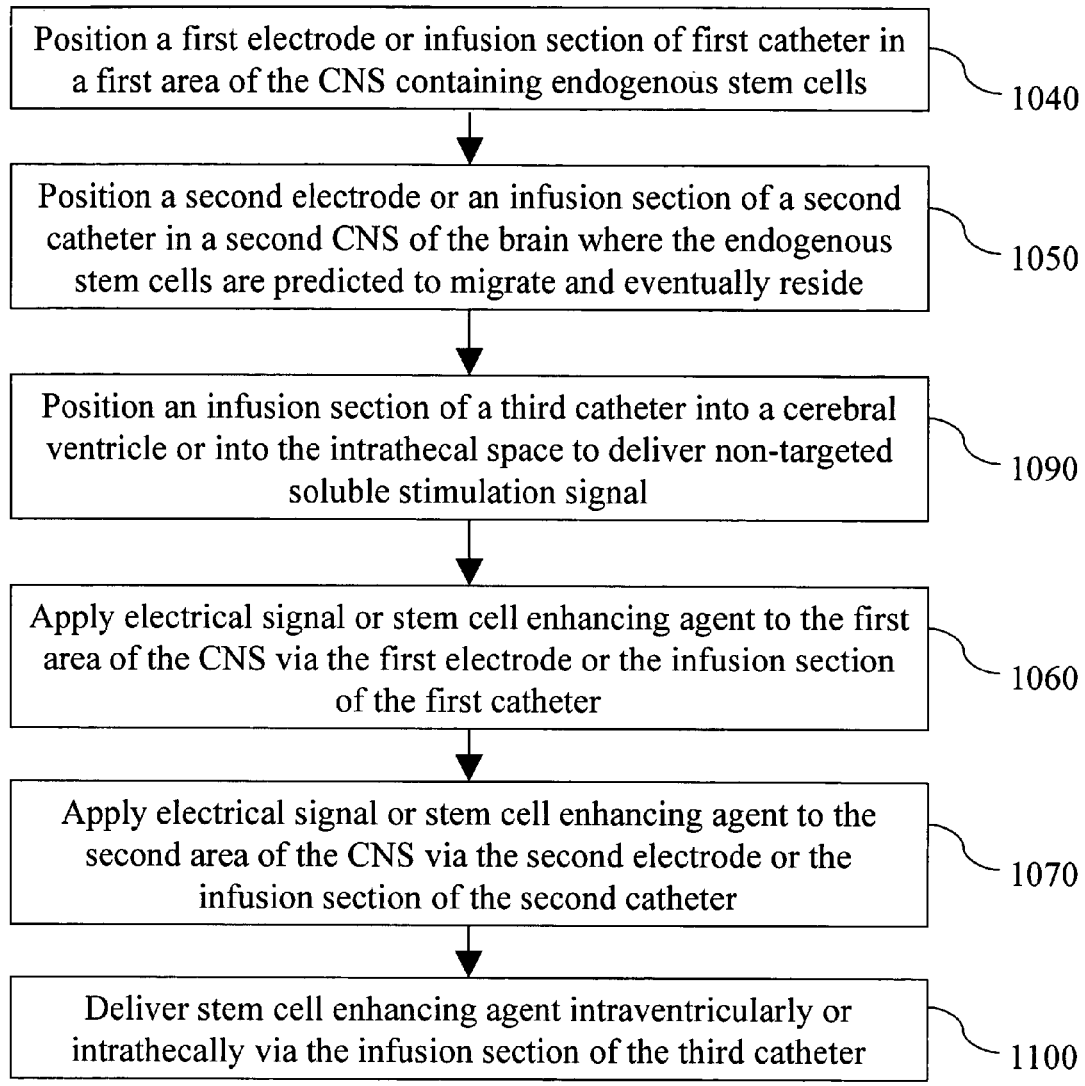

FIG. 8 refers to a method of achieving the treatment protocol as described in FIG. 6 or 7. An infusion section of a first catheter or a first electrode is positioned in a first area of the CNS containing endogenous stem cells (1040), and an infusion section of a second catheter or a second electrode is positioned in a second area of the CNS where the stem cells are predicted to migrate and eventually reside (1050). An electrical signal or stem cell enhancing agent is then applied to the first area of the CNS (1060) and the second area of the CNS (1070). As shown in FIG. 9, a stem cell enhancing agent may be delivered intraventricularly or intrathecally in a non targeted manner to enhance the treatment of the disease (1080). FIG. 10 depicts a method for carrying out the treatment protocol of FIG. 9. At 1090 a catheter an infusion section of a catheter is positioned into a cerebral ventricle or into the intrathecal space, and at 1100 a stem cell enhancing agent is delivered intraventricularly or intrathecally via the catheter.

Figure 11:
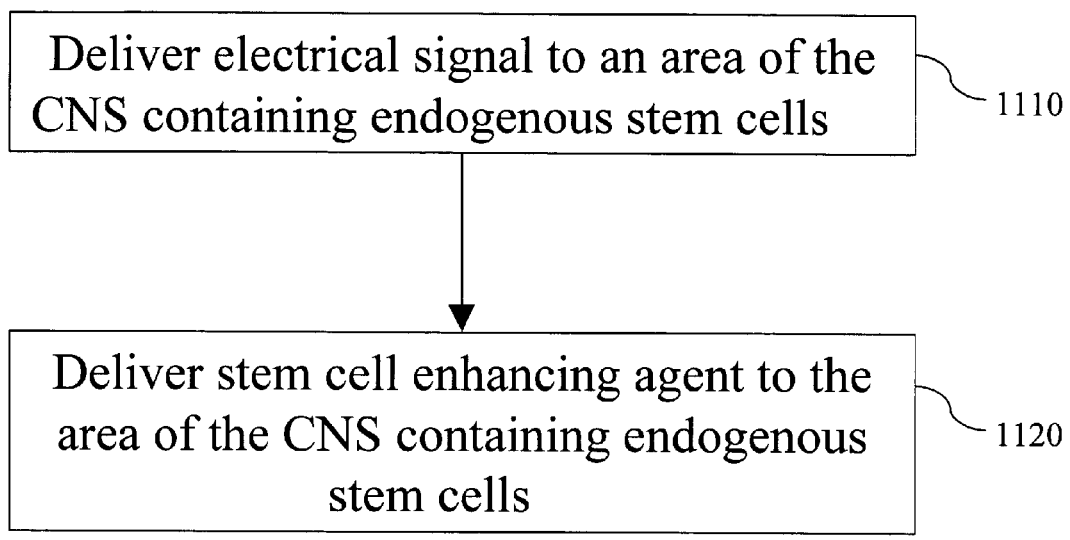
Figure 12:
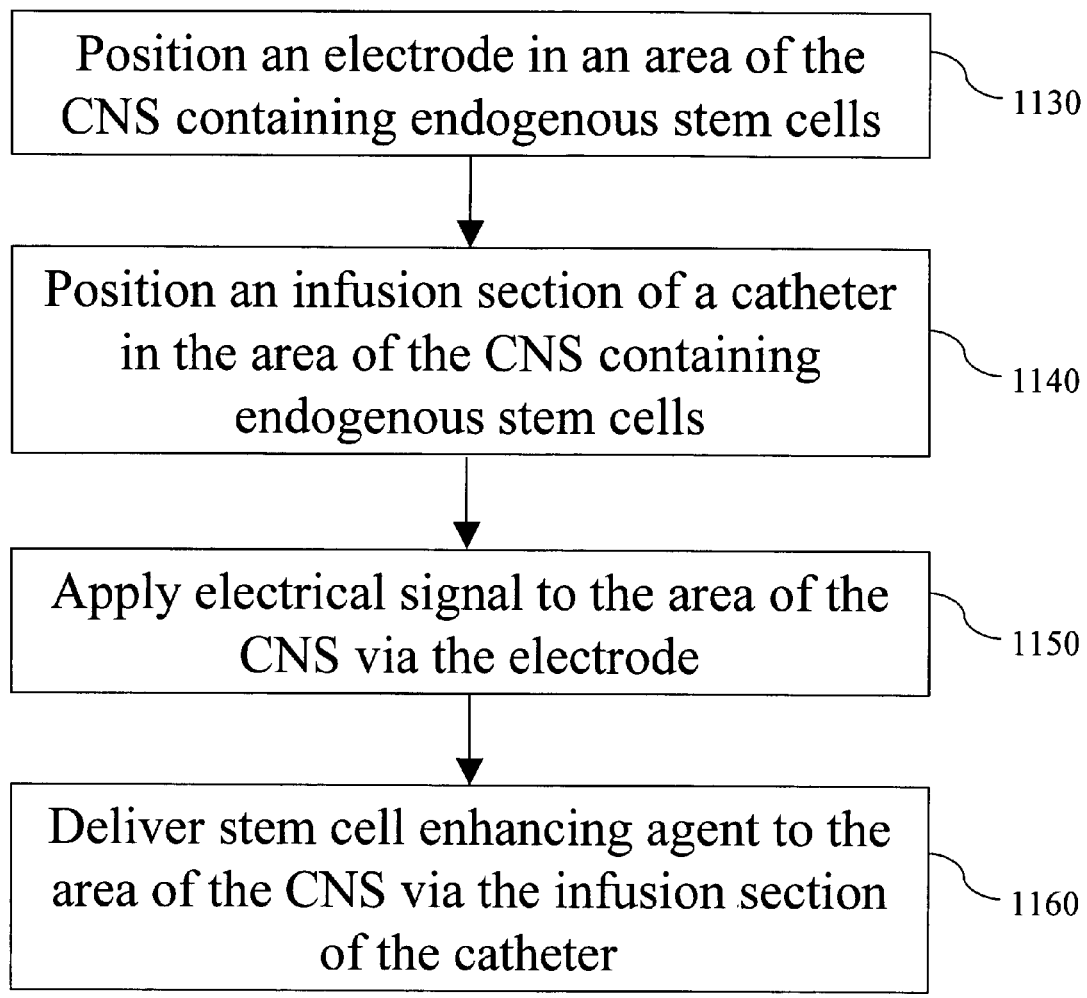

Referring to FIG. 11, an overview of a method of treating a disease associated with a loss of neuronal function is shown. As shown in FIG. 11, an electrical signal (1110) and a stem cell enhancing agent (1120) may be delivered to an area of the CNS containing endogenous stem cells. FIG. 12 depicts a method of achieving the treatment protocol as described in FIGS. 11. At 1130 an electrode is positioned in an area of the CNS containing endogenous stem cells. At 1140 an infusion section of a catheter is positioned in an area of the CNS containing endogenous stem cells. An electrical signal (1150) and a stem cell enhancing agent (1160) is applied to the area of the CNS.

Figure 13:
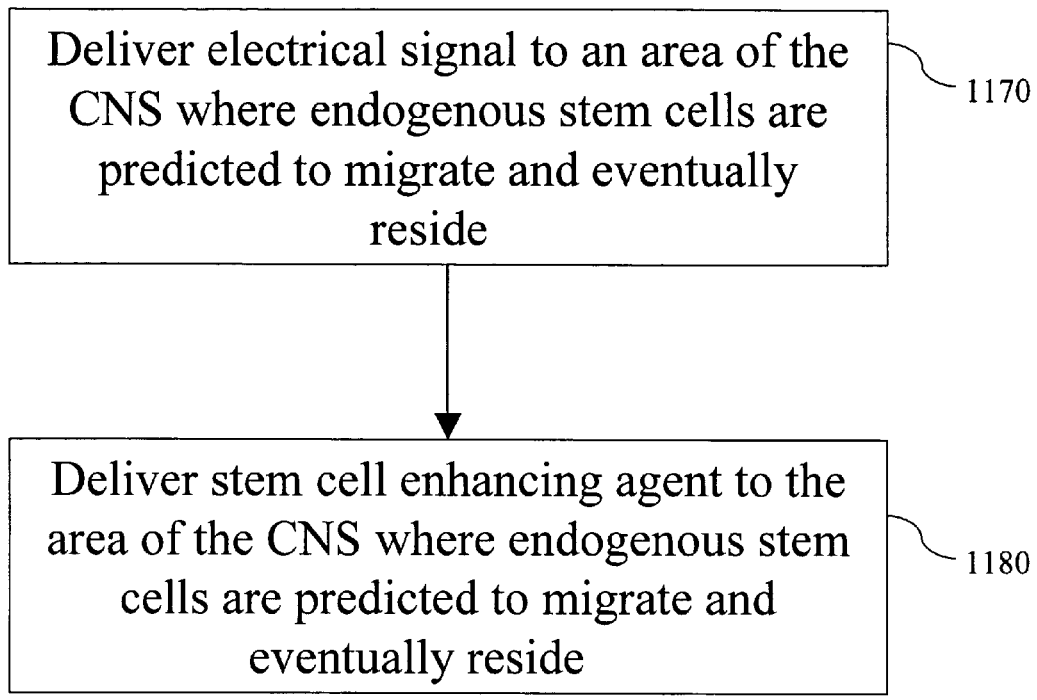
Figure 14:
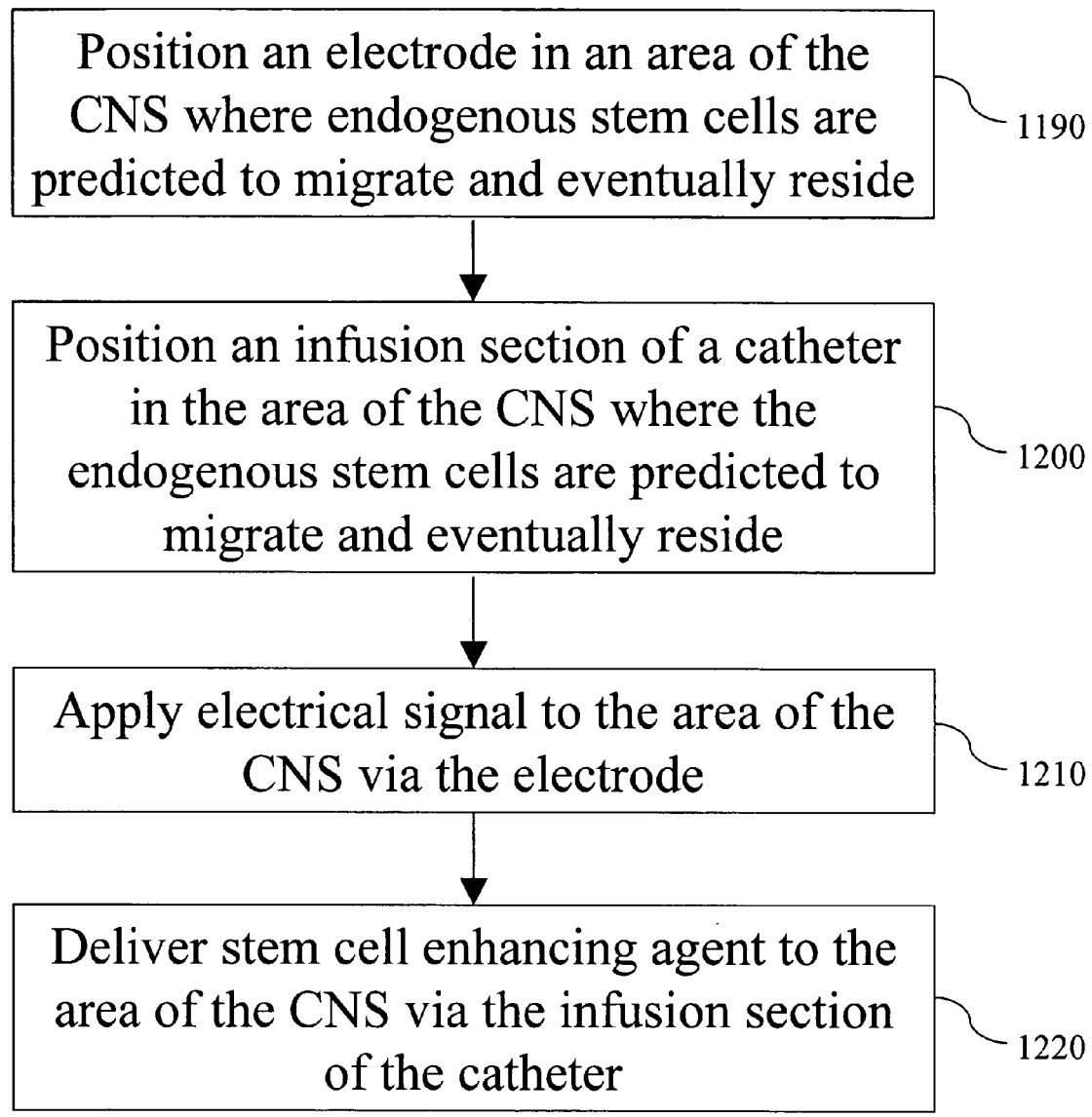

Referring to FIG. 13, an overview of a method of treating a disease associated with a loss of neuronal function is shown. As shown in FIG. 13, an electrical signal (1170) and a stem cell enhancing agent (1180) may be delivered to an area of the CNS where endogenous stem cells are predicted to migrate and eventually reside. FIG. 14 depicts a method of achieving the treatment protocol as described in FIGS. 12. At 1190 an electrode is positioned in an area of the CNS where endogenous stem cells are predicted to migrate and eventually reside. At 1200 an infusion section of a catheter is positioned in an area of the CNS where endogenous stem cells are predicted to migrate and eventually reside. An electrical signal (1210) and a stem cell enhancing agent (1220) is applied to the area of the CNS.

Figure 15:
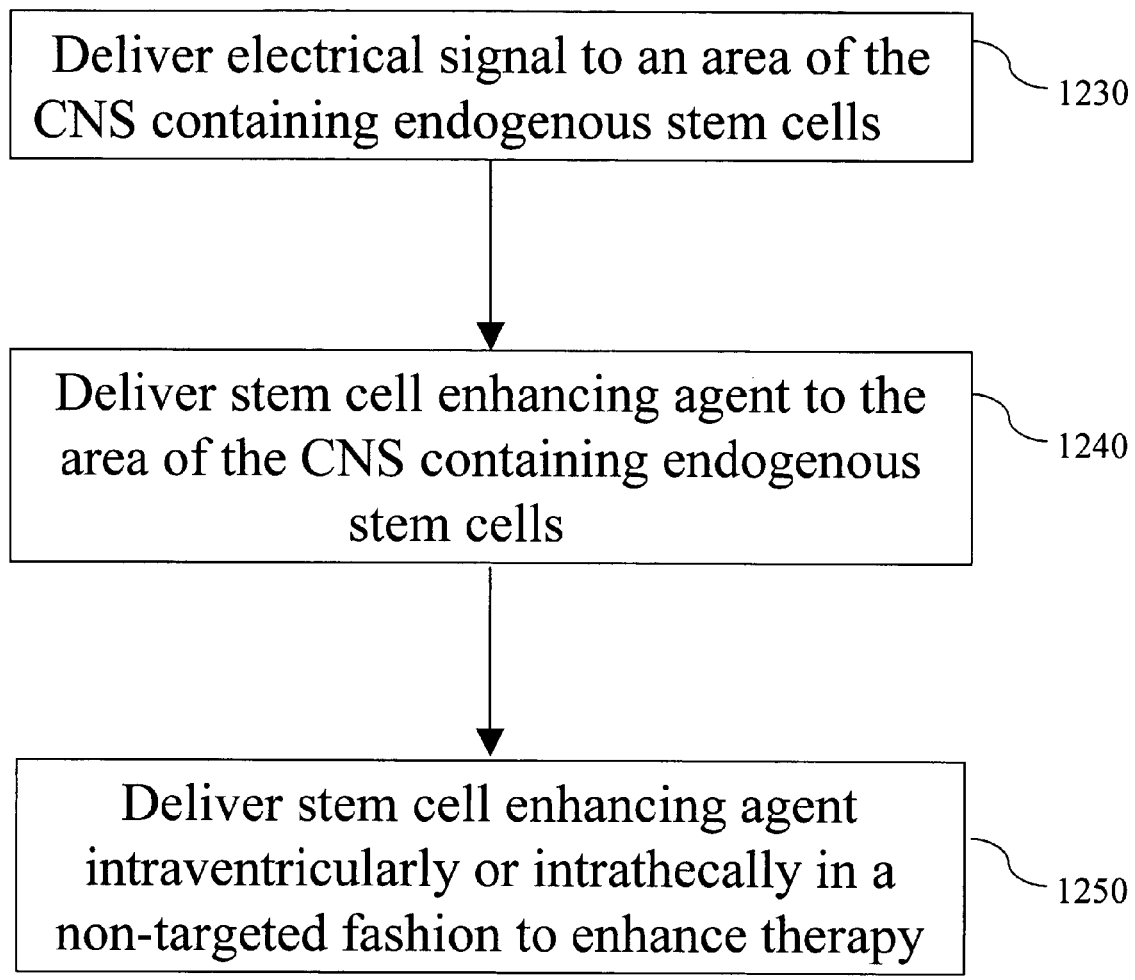

Referring to FIG. 15, an overview of a method of treating a disease associated with a loss of neuronal function is shown. An electrical signal is applied to an area of the CNS containing endogenous stem cells (1230), a stem cell enhancing agent is delivered to the area of the CNS containing endogenous stem cells (1240), and a stem cell enhancing agent is delivered intraventricularly or intrathecally (1250).

Figure 16:
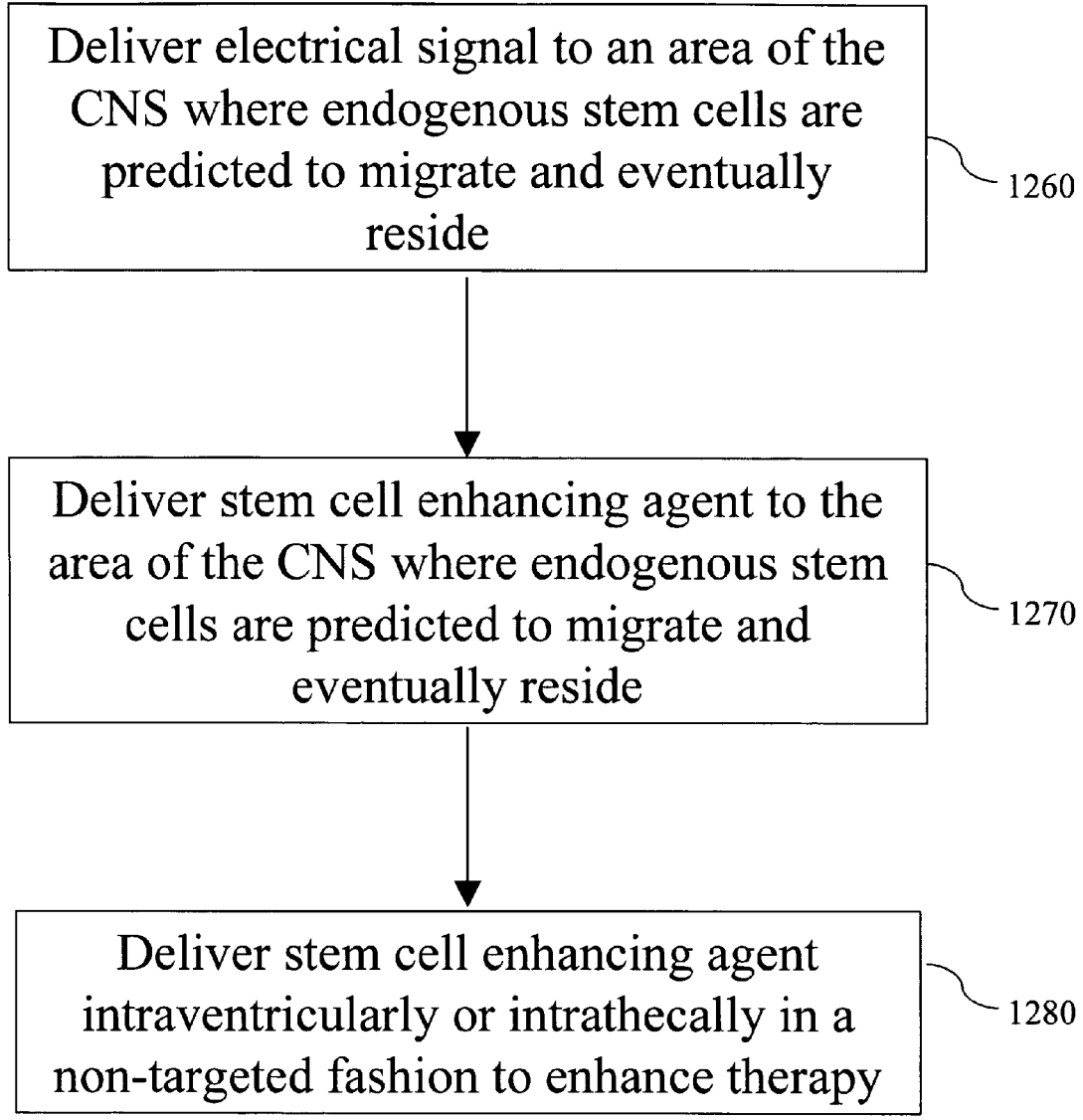

Referring to FIG. 16, an overview of a method of treating a disease associated with a loss of neuronal function is shown. An electrical signal is applied to an area of the CNS where endogenous stem cells are predicted to migrate and eventually reside (1260), a stem cell enhancing agent is delivered to the area of the CNS where endogenous stem cells are predicted to migrate and eventually reside (1270), and a stem cell enhancing agent is delivered intraventricularly or intrathecally (1280).

Other methods and combinations of steps shown in FIGS. 6-16 are contemplated. It will be understood that various steps as shown in FIGS. 6-16 may occur in any logical order and applications of various therapies can occur at the same or different times.

All printed publications, such as patents, patent applications, technical papers, and brochures, cited herein are hereby incorporated by reference herein, each in its respective entirety. As those of ordinary skill in the art will readily appreciate upon reading the description herein, at least some of the devices and methods disclosed in the patents and publications cited herein may be modified advantageously in accordance with the teachings of the present invention.

What is claimed is:

1. A method for alleviating damaged neural tissue or damaged glia cells subject in need thereof, comprising:
    implanting a first therapy delivery element comprising a therapy delivery region in the subject;
    positioning the therapy delivery region of the first therapy delivery element in a first CNS region containing endogenous stem cells selected from the group consisting of a subventricular zone of a lateral ventricle, a central canal of a spinal cord, a subgranular zone of the hippocampus;
    implanting a second therapy delivery element comprising a therapy delivery region in the subject;
    positioning the therapy delivery region of the second therapy delivery element in a second CNS region having the damaged neural tissue or glial cells;
    applying a first therapy to the first CNS region via the therapy delivery region of the first therapy delivery element, the first therapy configured to promote the endogenous stem cells to proliferate, migrate, or differentiate, the first therapy including (i) an electrical signal having a frequency of between about 1 Hz and 150 Hz, or (ii) a therapeutic agent selected from the group consisting of ciliary neurotrophic factor (CNTF), glial-derived neurotrophic factor (GDNF), brain-derived neurotrophic factor (BDNF), fibroblast growth factor (FGF), vascular endothelial growth factor (VEGF), neurotrophin-3 (NT-3), transforming growth factor-alpha (TGF-alpha), epidermal growth factor (EGF), insulin-like growth factor-1 (IGF-1), neurotrophin-4 (NT-4), neurotrophin-5 (NT-5), bone morphogenic protein (BMP), stromal cell factor (SCF), and anti-Nogo-A antibody; and
    applying a second therapy to the second CNS region via the therapy delivery region of the second therapy delivery element, the second therapy including (i) an electrical signal having a frequency of between about 1 Hz and 150 Hz, or (ii) a therapeutic agent selected from the group consisting of CNTF, GDNF, BDNF, FGF, VEGF, NT-3, TGF-alpha, EGF, IGF-1, NT-4, NT-5, EGF, BMP, and SCF, anti-Nogo-A antibody,
    wherein the first therapy delivery element is a catheter or a lead and the therapy delivery region of the first therapy element is an infusion section or an electrode,
    wherein the second therapy delivery element is a catheter or a lead and the therapy delivery region of the second therapy delivery element is an infusion section or an electrode, and
    wherein the first therapy and the second therapy are the same or different.

2. The method of claim 1, wherein at least one of the first and second therapy delivery elements is a lead.

3. The method of claim 2 further comprising implanting an electrical signal generator in the subject and operably coupling the lead to the electrical signal generator.

4. The method of claim 1, wherein at least one of the first and second therapy delivery elements is a catheter.

5. The method of claim 4, further comprising implanting a pump system in the subject and operably coupling the catheter to the pump system.

6. The method of claim 5, implanting the pump system comprises implanting a programmable pump system.

7. The method of claim 1, wherein the first CNS region is a mediolateral wall of a lateral ventricle.

8. The method of claim 1, further comprising delivering a growth factor or an inhibitor of a growth inhibitory molecule intraventricularly or intrathecally in a non-targeted manner, wherein the growth factor or inhibitor of a growth inhibitory molecule is selected from the group consisting of CNTF, GDNF, BDNF, FGF, VEGF, NT-3, TGF-alpha, EGF, IGF-1, NT-4, NT-5, EGF, BMF and SCF, anti-Nogo-A antibody.

9. The method of claim 1, wherein the subject is suffering from a disease selected from Parkinson's disease, Alzheimer's disease, spinal cord injury, and traumatic brain injury.

10. A method for alleviating damaged neural tissue or damaged glia cells subject in need thereof, comprising:
implanting a lead comprising an electrode within a subject;
positioning the electrode in communication with a CNS region containing endogenous stem cells selected from the group consisting of a subventricular zone of a lateral ventricle, a central canal of a spinal cord, a subgranular zone of the hippocampus;
implanting a catheter comprising an infusion section within the subject;
positioning the infusion section in communication with the CNS region containing the endogenous stem cells;
applying via the electrode an electrical signal having a frequency of between about 1 Hz and 150 Hz via the electrode to the CNS region containing the endogenous stem cells; and
applying via the infusion section of the catheter a therapeutic agent selected from the group consisting of CNTF, GDNF, BDNF, FGF, VEGF, NT-3, TGF-alpha, EGF, IGF-1, NT-4, NT-5, EGF, BMP, SCF, and anti-Nogo-A antibody via the infusion section to the CNS region containing the endogenous stem cells,
wherein the electrical stimulation and the therapeutic agent promote one or more of:
(a) proliferation of the endogenous stem cells;
(b) migration of the endogenous stem cells; and
(c) differentiation of the endogenous stem cells.

11. The method of claim 10, further comprising delivering a growth factor or an inhibitor of a growth inhibitory molecule intraventriculary or intrathecally in a non-targeted manner, wherein the growth factor or inhibitor of a growth inhibitory molecule is selected from the group consisting of CNTF, GDNF, BDNF, FGF, VEGF, NT-3, TGF-alpha, EGF, IGF-1, NT-4, NT-5, EGF, BMP, and SCF, anti-logo-A antibody.

12. The method of claim 11, wherein the growth factor or inhibitor of a growth inhibitory molecule is selected from the. group consisting of GDNF, BDNF, FGF, VEGF, NT-3, TGF-alpha, EGF, IGF-1, CNTF, and an anti-Nogo-A. antibody.

13. The method of claim 11, wherein the electrical signal is a depolarizing signal.

14. The method of claim 11, wherein the subject is suffering from a disease selected from Parkinson's disease, Alzheimer's disease, spinal cord injury, and traumatic brain injury.

15. A method for alleviating damaged neural tissue or damaged glia cells subject in need thereof comprising:
implanting a lead comprising an electrode in a subject;
positioning the electrode in a CNS region having the damaged neural tissue or damaged glial cells;
implanting a catheter comprising an infusion section in the subject;
positioning the intbsion section in a CNS region containing endogenous stem cells selected from the group consisting of a subventricular zone of a lateral ventricle, a central canal of a spinal cord, a subgranular zone of the hippocampus;
applying via the electrode an electrical signal having a frequency of between about 1 Hz and 150 Hz to the CNS region; and
applying via the infusion section of the catheter a therapeutic agent selected from the group consisting of CNTF, GDNF, BDNF, FGF, VEGF, NT-3, TGF-alpha, EGF, IGF-1, NT-4, NT-5, EGF, EMP, and SCF, anti-Nogo-A antibody to the CNS region,
wherein the electrical signal and the therapeutic agent promote one or more of
(a) proliferation of endogenous stem cells;
(b) migration of endogenous stem cells to the CNS region;
(c) differentiation of endogenous stem cells; and
(d) integration of endogenous stem cells in the CNS region.

16. The method of claim 15, further comprising delivering a growth factor or an inhibitor of a growth inhibitory molecule intrayentriculary or intrathecally in a non-targeted manner, wherein the growth factor or inhibitor of a growth inhibitory molecule is selected from the group consisting of CNTF, GDNF, BDNF, FGF, VEGF, NT-3, TGF-alpha, EGF, IGF-1, NT-4, NT-5, EGF, BMP, and SCF, anti-Nogo-A antibody.

17. The method of claim 15, wherein the growth factor or inhibitor of a growth inhibitory molecule is selected from the group consisting of GDNF, BDNF, FGF, VEGF, NT-3, TGF-alpha, EGF, IGF-1, CNTF, and an anti-Nogo-A antibody.

18. The method of claim 15, wherein the subject is suffering from a disease selected from Parkinson's disease, Alzheimer's disease, spinal cord injury, and traumatic brain injury.

19. A method for alleviating damaged neural tissue or damaged glia cells subject in need thereof; comprising:
implanting a lead comprising an electrode in a subject;
positioning the electrode in a first CNS region containing endogenous stem cells, wherein the first CNS region containing endogenous stem cells is selected from the group consisting of a subventricular zone of a lateral ventricle, a central canal of a spinal cord, a subgranular zone of the hippocampus;
implanting a catheter comprising an infusion section in the subject;
positioning the infusion section in a second CNS region having the damaged neural tissue or damaged glia cells;
applying a first therapy to the first CNS region via the electrode of the lead, the first therapy including an electrical signal having a frequency of between about 1 Hz and 150 Hz; and
applying a second therapy to the second CNS region via the infusion section of the catheter, the second therapy including a therapeutic agent selected from the group consisting of CNTF, GDNF, BDNF, FGF, VEGF, NT-3, TGF-alpha, EGF, IGF-1, NT-4, NT-5, EGF, BMP, and SCE, anti-Nogo-A antibody,
wherein the electrical signal and the therapeutic agent promote one or more of:
(a) proliferation of endogenous stern cells;
(b) migration of endogenous stern cells to the CNS region;
(c) differentiation of endogenous stem cells; and
(d), integration of endogenous stem cells in the CNS region.

20. The method of claim 19, wherein the subject is suffering from a disease selected from Parkinson's disease, Alzheimer's disease, spinal cord injury, and traumatic brain injury.

* * * * *